United States Patent
Hassanein et al.

(10) Patent No.: US 9,457,179 B2
(45) Date of Patent: Oct. 4, 2016

(54) SYSTEMS FOR MONITORING AND APPLYING ELECTRICAL CURRENTS IN AN ORGAN PERFUSION SYSTEM

(75) Inventors: Waleed Hassanein, North Andover, MA (US); Ahmed Elbetanony, North Andover, MA (US); Richard Bringham, North Andover, MA (US); Robert Havener, Lynnfield, MA (US); Vincent Lambert, II, Salisbury, MA (US); Burt Ochs, Andover, MA (US)

(73) Assignee: TRANSMEDICS, INC., Andover, MA (US)

( * ) Notice: Subject to any disclaimer, the term of this patent is extended or adjusted under 35 U.S.C. 154(b) by 1463 days.

(21) Appl. No.: 11/822,495

(22) Filed: Jul. 6, 2007

(65) Prior Publication Data

US 2008/0234768 A1    Sep. 25, 2008

Related U.S. Application Data

(60) Provisional application No. 60/919,306, filed on Mar. 20, 2007.

(51) Int. Cl.
| | |
|---|---|
| *A01N 1/00* | (2006.01) |
| *A01N 1/02* | (2006.01) |
| *C12M 1/36* | (2006.01) |
| *C12M 1/38* | (2006.01) |
| *C12M 3/00* | (2006.01) |

(Continued)

(52) U.S. Cl.
CPC ............ *A61N 1/0492* (2013.01); *A61N 1/046* (2013.01); *A61N 1/0488* (2013.01)

(58) Field of Classification Search
USPC ...... 435/284.1, 286.5, 286.6, 307.1; 600/36; 623/915, 916, 921, 922
See application file for complete search history.

(56) References Cited

U.S. PATENT DOCUMENTS

| | | | |
|---|---|---|---|
| 3,253,595 A | * | 5/1966 | Murphy, Jr. et al. ......... 607/129 |
| 3,388,803 A | | 6/1968 | Scott |
| 3,406,531 A | | 10/1968 | Swenson et al. |

(Continued)

FOREIGN PATENT DOCUMENTS

| | | |
|---|---|---|
| CN | 1232723 A | 10/1999 |
| DE | 4201259 A1 | 7/1993 |

(Continued)

OTHER PUBLICATIONS

"2002 Design & Engineering Awards, Portable Organ Preservation System," Science (2002).

(Continued)

*Primary Examiner* — Nathan Bowers
*Assistant Examiner* — Lydia Edwards
(74) *Attorney, Agent, or Firm* — Wilmer Cutler Pickering Hale and Dorr LLP

(57) ABSTRACT

Electrode systems have been developed for use in perfusion systems to measure the electrical activity of an explanted heart and to provide defibrillation energy as necessary. The perfusion systems maintain the heart in a beating state at, or near, normal physiological conditions; circulating oxygenated, nutrient enriched perfusion fluid to the heart at or near physiological temperature, pressure and flow rate. These systems include a pair of electrodes that are placed epicardially on the right atrium and left ventricle of the explanted heart, as well as an electrode placed in the aortic blood path.

33 Claims, 9 Drawing Sheets

(51) Int. Cl.
*A61F 2/00* (2006.01)
*A61N 1/04* (2006.01)

(56) References Cited

U.S. PATENT DOCUMENTS

| | | |
|---|---|---|
| 3,468,136 A | 9/1969 | Whittington |
| 3,537,956 A | 11/1970 | Falcone |
| 3,545,221 A | 12/1970 | Swenson et al. |
| 3,545,605 A | 12/1970 | Robins |
| 3,587,567 A * | 6/1971 | Schiff .................... 601/21 |
| 3,607,646 A | 9/1971 | de Roissart |
| 3,632,473 A | 1/1972 | Belzer et al. |
| 3,639,084 A | 2/1972 | Goldhaber |
| 3,654,085 A | 4/1972 | Norr et al. |
| 3,738,914 A | 6/1973 | Thorne et al. |
| 3,772,153 A | 11/1973 | De Roissart |
| 3,777,507 A | 12/1973 | Burton et al. |
| 3,843,455 A | 10/1974 | Bier |
| 3,851,646 A | 12/1974 | Sarns |
| 3,881,990 A | 5/1975 | Burton et al. |
| 3,995,444 A | 12/1976 | Clark et al. |
| 4,186,565 A | 2/1980 | Toledo-Pereyra |
| 4,231,354 A | 11/1980 | Kurtz et al. |
| 4,415,556 A | 11/1983 | Bretschneider et al. |
| 4,598,697 A | 7/1986 | Numazawa et al. |
| 4,605,644 A | 8/1986 | Foker |
| 4,666,425 A | 5/1987 | Fleming |
| 4,719,201 A | 1/1988 | Foker |
| 4,723,939 A | 2/1988 | Anaise |
| 4,745,759 A | 5/1988 | Bauer et al. |
| 4,759,371 A | 7/1988 | Franetzki |
| 4,847,470 A | 7/1989 | Bakke |
| 4,920,044 A | 4/1990 | Bretan, Jr. |
| 5,051,352 A | 9/1991 | Martindale et al. |
| 5,066,578 A | 11/1991 | Wikman-Coffelt |
| 5,141,847 A | 8/1992 | Sugimachi et al. |
| 5,145,771 A | 9/1992 | Lemasters et al. |
| 5,157,930 A | 10/1992 | McGhee et al. |
| 5,200,398 A | 4/1993 | Strasberg et al. |
| 5,217,860 A | 6/1993 | Fahy et al. |
| 5,285,657 A | 2/1994 | Bacchi et al. |
| 5,306,711 A | 4/1994 | Andrews |
| 5,326,706 A | 7/1994 | Yland et al. |
| 5,338,662 A | 8/1994 | Sadri |
| 5,356,593 A | 10/1994 | Heiberger et al. |
| 5,356,771 A | 10/1994 | O'Dell |
| 5,362,622 A | 11/1994 | O'Dell et al. |
| 5,370,989 A | 12/1994 | Stern et al. |
| 5,381,510 A | 1/1995 | Ford et al. |
| 5,385,821 A | 1/1995 | O'Dell et al. |
| 5,395,314 A | 3/1995 | Klatz et al. |
| 5,405,742 A | 4/1995 | Taylor |
| 5,407,669 A | 4/1995 | Lindstrom et al. |
| 5,407,793 A | 4/1995 | Del Nido et al. |
| 5,472,876 A | 12/1995 | Fahy |
| 5,473,791 A | 12/1995 | Holcomb et al. |
| 5,494,822 A | 2/1996 | Sadri |
| 5,498,427 A | 3/1996 | Menasche et al. |
| 5,505,709 A | 4/1996 | Funderburk et al. |
| 5,514,536 A | 5/1996 | Taylor |
| 5,552,267 A | 9/1996 | Stern et al. |
| 5,554,123 A | 9/1996 | Herskowitz |
| 5,554,497 A | 9/1996 | Raymond |
| 5,571,801 A | 11/1996 | Segall et al. |
| 5,584,804 A | 12/1996 | Klatz et al. |
| 5,586,438 A * | 12/1996 | Fahy .................... 62/78 |
| 5,588,816 A | 12/1996 | Abbott et al. |
| 5,599,173 A | 2/1997 | Chen et al. |
| 5,599,659 A | 2/1997 | Brasile et al. |
| 5,613,944 A | 3/1997 | Segall et al. |
| 5,643,712 A | 7/1997 | Brasile |
| 5,656,420 A | 8/1997 | Chien |
| 5,679,565 A | 10/1997 | Mullen et al. |
| 5,693,462 A | 12/1997 | Raymond |
| 5,698,536 A | 12/1997 | Segall et al. |
| 5,699,793 A | 12/1997 | Brasile |
| 5,702,881 A | 12/1997 | Brasile et al. |
| 5,716,378 A * | 2/1998 | Minten .................... 607/3 |
| 5,723,281 A | 3/1998 | Segall et al. |
| 5,733,894 A | 3/1998 | Segall et al. |
| 5,747,071 A | 5/1998 | Segall et al. |
| 5,752,929 A | 5/1998 | Klatz et al. |
| 5,770,149 A | 6/1998 | Raible |
| 5,776,063 A | 7/1998 | Dittrich et al. |
| 5,786,136 A | 7/1998 | Mayer et al. |
| 5,787,544 A | 8/1998 | Meade |
| 5,807,737 A | 9/1998 | Schill et al. |
| 5,823,799 A | 10/1998 | Tor et al. |
| 5,843,024 A | 12/1998 | Brasile |
| 5,856,081 A | 1/1999 | Fahy |
| 5,882,328 A | 3/1999 | Levy et al. |
| 5,965,433 A | 10/1999 | Gardetto et al. |
| 5,998,240 A | 12/1999 | Hamilton et al. |
| 6,024,698 A | 2/2000 | Brasile |
| 6,034,109 A | 3/2000 | Ramasamy et al. |
| 6,042,550 A | 3/2000 | Haryadi et al. |
| 6,046,046 A | 4/2000 | Hassanein |
| 6,050,987 A | 4/2000 | Rosenbaum |
| 6,100,082 A | 8/2000 | Hassanein |
| 6,110,139 A | 8/2000 | Loubser |
| 6,110,504 A | 8/2000 | Segall et al. |
| 6,144,444 A | 11/2000 | Haworth et al. |
| 6,168,877 B1 | 1/2001 | Pedicini et al. |
| 6,365,338 B1 | 4/2002 | Bull et al. |
| 6,375,611 B1 | 4/2002 | Voss et al. |
| 6,375,613 B1 | 4/2002 | Brasile |
| 6,389,308 B1 | 5/2002 | Shusterman |
| 6,475,716 B1 | 11/2002 | Seki et al. |
| 6,490,880 B1 | 12/2002 | Walsh |
| 6,492,103 B1 | 12/2002 | Taylor |
| 6,492,745 B1 | 12/2002 | Colley, III et al. |
| 6,524,785 B1 | 2/2003 | Cozzone et al. |
| 6,569,615 B1 | 5/2003 | Thatte et al. |
| 6,582,953 B2 | 6/2003 | Brasile |
| 6,600,941 B1 | 7/2003 | Khuri |
| 6,609,987 B1 | 8/2003 | Beardmore |
| 6,631,830 B2 | 10/2003 | Ma et al. |
| 6,642,045 B1 | 11/2003 | Brasile |
| 6,673,594 B1 | 1/2004 | Owen et al. |
| 6,696,238 B2 | 2/2004 | Murphy et al. |
| 6,783,328 B2 | 8/2004 | Lucke et al. |
| 6,792,309 B1 * | 9/2004 | Noren .................... 607/23 |
| 6,794,124 B2 | 9/2004 | Steen et al. |
| 6,811,965 B2 | 11/2004 | Vodovotz et al. |
| 6,878,339 B2 | 4/2005 | Akiyama et al. |
| 6,925,324 B2 | 8/2005 | Shusterman |
| 6,953,655 B1 | 10/2005 | Hassanein et al. |
| 6,974,436 B1 | 12/2005 | Aboul-Hosn et al. |
| 7,001,354 B2 | 2/2006 | Suzuki et al. |
| 7,008,380 B1 | 3/2006 | Rees et al. |
| 7,238,165 B2 | 7/2007 | Vincent et al. |
| 7,316,666 B1 | 1/2008 | Entenman et al. |
| 7,452,711 B2 | 11/2008 | Daykin |
| 7,572,622 B2 | 8/2009 | Hassanein et al. |
| 7,651,835 B2 | 1/2010 | Hassanein et al. |
| 8,304,181 B2 | 11/2012 | Hassanein et al. |
| 8,409,846 B2 | 4/2013 | Hassanein et al. |
| 8,420,380 B2 | 4/2013 | Fishman et al. |
| 8,465,970 B2 | 6/2013 | Hassanein et al. |
| 8,535,934 B2 | 9/2013 | Hassanein et al. |
| 8,585,380 B2 | 11/2013 | Hassanein et al. |
| 2001/0003652 A1 | 6/2001 | Freeman |
| 2002/0012988 A1 | 1/2002 | Brasile |
| 2002/0102720 A1 | 8/2002 | Steen |
| 2002/0132220 A1 | 9/2002 | Berens et al. |
| 2002/0151950 A1 * | 10/2002 | Okuzumi .................... 607/142 |
| 2002/0164795 A1 | 11/2002 | Gen |
| 2002/0177117 A1 | 11/2002 | Wolf |
| 2003/0011604 A1 | 1/2003 | Capers |
| 2003/0040665 A1 | 2/2003 | Khuri et al. |
| 2003/0050689 A1 | 3/2003 | Matson |
| 2003/0053998 A1 | 3/2003 | Daemen et al. |
| 2003/0073227 A1 | 4/2003 | Hull et al. |
| 2003/0074760 A1 | 4/2003 | Keller |

(56) References Cited

U.S. PATENT DOCUMENTS

| | | |
|---|---|---|
| 2003/0086830 A1 | 5/2003 | Haywood et al. |
| 2003/0135152 A1 | 7/2003 | Kollar et al. |
| 2003/0147466 A1 | 8/2003 | Liang |
| 2004/0015042 A1 | 1/2004 | Vincent et al. |
| 2004/0017658 A1 | 1/2004 | Lo et al. |
| 2004/0018966 A1 | 1/2004 | Segall et al. |
| 2004/0029096 A1 | 2/2004 | Steen |
| 2004/0038192 A1 | 2/2004 | Brasile |
| 2004/0058432 A1 | 3/2004 | Owen et al. |
| 2004/0082057 A1 | 4/2004 | Alford et al. |
| 2004/0086578 A1 | 5/2004 | Segall et al. |
| 2004/0102415 A1 | 5/2004 | Thatte et al. |
| 2004/0102678 A1 | 5/2004 | Haindl |
| 2004/0106958 A1* | 6/2004 | Mathis et al. ............. 607/11 |
| 2004/0110800 A1 | 6/2004 | Bril et al. |
| 2004/0115689 A1 | 6/2004 | Augello et al. |
| 2004/0138542 A1 | 7/2004 | Khuri et al. |
| 2004/0168341 A1 | 9/2004 | Petersen et al. |
| 2004/0170950 A1 | 9/2004 | Prien |
| 2004/0171138 A1 | 9/2004 | Hassanein et al. |
| 2004/0202993 A1 | 10/2004 | Poo et al. |
| 2004/0224298 A1 | 11/2004 | Brassil et al. |
| 2004/0235142 A1 | 11/2004 | Schein et al. |
| 2004/0236170 A1 | 11/2004 | Kim |
| 2004/0248281 A1 | 12/2004 | Wright et al. |
| 2005/0010118 A1 | 1/2005 | Toyoda et al. |
| 2005/0019917 A1 | 1/2005 | Toledo-Pereyra et al. |
| 2005/0142532 A1 | 6/2005 | Poo et al. |
| 2005/0147958 A1 | 7/2005 | Hassanein et al. |
| 2005/0153271 A1 | 7/2005 | Wenrich |
| 2005/0170019 A1 | 8/2005 | Roth |
| 2005/0182349 A1 | 8/2005 | Linde et al. |
| 2005/0187469 A1 | 8/2005 | Phillips |
| 2006/0039870 A1 | 2/2006 | Turner |
| 2006/0074470 A1* | 4/2006 | Bartels et al. ............. 607/119 |
| 2006/0121438 A1 | 6/2006 | Toledo-Pereyra et al. |
| 2006/0124130 A1 | 6/2006 | Bonassa |
| 2006/0134073 A1 | 6/2006 | Naka et al. |
| 2006/0148062 A1 | 7/2006 | Hassanein et al. |
| 2006/0154357 A1 | 7/2006 | Hassanein et al. |
| 2006/0154359 A1 | 7/2006 | Hassanein et al. |
| 2006/0160204 A1 | 7/2006 | Hassanein et al. |
| 2006/0292544 A1 | 12/2006 | Hassanein et al. |
| 2007/0196461 A1 | 8/2007 | Weers |
| 2008/0017194 A1 | 1/2008 | Hassanein et al. |
| 2008/0234768 A1 | 9/2008 | Hassanein et al. |
| 2008/0286746 A1 | 11/2008 | Poo et al. |
| 2009/0142830 A1 | 6/2009 | Yamashiro et al. |
| 2009/0143417 A1 | 6/2009 | Smith et al. |
| 2009/0197240 A1 | 8/2009 | Fishman et al. |
| 2009/0197292 A1 | 8/2009 | Fishman et al. |
| 2009/0197324 A1 | 8/2009 | Fishman et al. |
| 2009/0197325 A1 | 8/2009 | Fishman et al. |
| 2009/0215022 A1 | 8/2009 | Page et al. |
| 2009/0312724 A1 | 12/2009 | Pipkin et al. |
| 2011/0136096 A1 | 6/2011 | Hassanein et al. |
| 2011/0190572 A1 | 8/2011 | Brophy et al. |
| 2013/0011823 A1 | 1/2013 | Hassanein et al. |
| 2013/0078710 A1 | 3/2013 | Hassanein et al. |
| 2013/0157248 A1 | 6/2013 | Fishman et al. |
| 2013/0295552 A1 | 11/2013 | Hassanein et al. |

FOREIGN PATENT DOCUMENTS

| | | |
|---|---|---|
| DE | 10121159 A1 | 11/2002 |
| DK | 4201259 | 7/1993 |
| EP | 0347923 | 12/1989 |
| EP | 0376763 | 7/1990 |
| EP | 1942726 A2 | 7/2008 |
| JP | H02-306901 A | 12/1990 |
| JP | 04-099701 A | 3/1992 |
| JP | 2001061956 A | 3/2001 |
| JP | 2004513889 A | 5/2004 |
| JP | 2004525290 A | 8/2004 |
| JP | 2004529938 A | 9/2004 |
| JP | 2009-521931 A | 6/2009 |
| JP | 2011-511000 A | 4/2011 |
| WO | WO-8805261 | 7/1988 |
| WO | WO 8805261 A1 * | 7/1988 |
| WO | WO-9531897 | 11/1995 |
| WO | WO-9618293 | 6/1996 |
| WO | WO-9629865 | 10/1996 |
| WO | WO-9746091 | 12/1997 |
| WO | WO-9915011 | 4/1999 |
| WO | WO-0060936 A1 | 10/2000 |
| WO | WO-2004026031 A2 | 4/2004 |
| WO | WO-2006042138 A2 | 4/2006 |
| WO | WO-2006124820 A2 | 11/2006 |
| WO | WO-2007079185 A2 | 7/2007 |
| WO | WO-2008106724 A1 | 9/2008 |

OTHER PUBLICATIONS

Ahmad, et al., "A Pathophysiologic Study of the Kidney Tubule to Optimize Organ Preservation Solutions," Kidney Int. 66(1):77-90 (2004).

Anathaswamy, "Machine Keeps Organs Alive for Longer," New Scientist.com (2002).

Aoki, M. et al. "Anti-CD18 Attenuates Deleterious Effects of Cardiopulmonary Bypass and Hypothermic Circulatory Arrest in Piglets," J. Card. Surg. 10:407-17 (1995).

Bando, et al., "Oxygenated Perfluorocarbon, Recombinant Human Superoxide Dismutase, and Catalase Ameliorate Free Radical Incuded Myocardial Injury During Heart Preservation and Transplantation," J. Thorac Cardiovasc Surb. 96:930-8 (Dec. 1988).

Belzer, "Formula for Belzer MPS Solution," University of Wisconsin-Madison Organ Preservation (internet reference) (2003).

Benichou, et al., "Canine and Human Liver Preservation for 6 to 18 Hours by Cold Infusion," Transplation, 24(6):407-411 (Dec. 1977).

Birkett et al., "The Fatty Acid Content and Drug Binding Characteristics of Commercial Albumin Preparations," Clin. Chem. Acta. 85:253-258 (1978).

Blanchard, et al., "Techniques for Perfusion and Storage of Heterotopic Heart Transplants in Mice," Microsurgery, 6:169-174 (1985).

Boggi, et al., "Pancreas Preservation with University of Wisconsin and Celsior Solutions," Transplant Proc. 36(3):563-5 (2004).

Boggi, et al., "Pancreas Preservation with University of Wisconsin and Celsior Solutions: A Single-Center Prospective, Randomized Pilot Study," Transplantation 27:77(8):1186-90 (2004).

Boyle, Jr. et al., "Ischemia-Reperfusion Injury," Ann. Thorac. Surg. 64:524-30 (1997).

Burt, et al, "Myocardial Function After Preservation for 24 Hours," Jour. Thorac. and Cardiovascular Surg., 92(2):238-46 (1986).

Brasile, et al., "Organ Preservation Without Extreme Hypothermia Using an Oxygen Supplemented Perfusate," Art. Cells. Blood Subs. and Immob. Biotech., 22(4):1463-68 (1994).

Calhoon, et al., "Twelve-Hour Canine Heart Preservation With a Simple, Portable Hypothermic Organ Perfusion Device," Ann. Thorac. Surg., 62:91-3 (1996).

Canelo R., et al., "Experience with Hystidine Tryptophan Ketoglutarate Versus University Wisconsin Preservation Solutions in Transplatation," Int. Surg. 88(3):145-51 (2003).

"CELSIOR Cold Storage Solution," Sangstat Medical Corporation (internet reference) (1999).

Chambers, et al., "Long-Term Preservation of the Heart: The Effect of Infusion Pressure During Continuous Hypothermic Cardioplegia," Jour. of Heart and Lung Transp., 11(4):665-75 (1992).

Chen, et al., "Development of New Organ Preservation Solutions in Kyoto University," Yonsei Medical Journal, 46(6):1107-40 (2004).

Chien, et al., "A Simple Technique for Multiorgan Preservation," Jour. of Thor. and Card. Surg., 95(1):55-61 (1988).

Chien, et al., Canine Lung Transplantation After More Than Twenty-four Hours of Normothermic Preservation, J. Heart Lung Transplant, 16:3340-51 (1997).

(56) References Cited

OTHER PUBLICATIONS

Chien, et al., "Functional Studies of the Heart During a 24-Hour Preservation Using a New Autoperfusion Preparation," The Journal of Heart and Lung Transplantation, 10(3):401-8 (1991).
Cimino, Adria, "Doctor Develops Device to Preserve Donated Organs," Mass High Tech (2001).
Christophi, et al., "A Comparison of Standard and Rapid Infusion Methods of Liver Preservation During Multi-Organ Procurement," Aust. N.Z.J. Surg., 61(9):692-94 (1991).
Collins, B.H., "Organ Transplantation: What Is the State of the Art?," Ann. Surg., 238(6 Suppl):S72-89 (2003).
Cronin, et al., "Liver Transplantation at the University of Chicago," Clin. Transpl. 231-8 (1999).
Daemen, et al., "Short-Term Outcome of Kidney Transplants Fron Non-Heart-Beating Donors After Preservation by Machine Perfusion," Transpl. Int. 9(Supp 1):S76-S80 (1996).
Demertzis et al., "University of Wisconsin Versus St. Thomas' Hospital Solution for Human Donor Heart Preservation," Ann. Thorac. Surg. 55:1131-7 (1993).
Den Butter, et al., "Comparison of Solutions for Preservation of the Rabbit Liver as Tested by Isolated Perfusion," Transpl. Int. 8(6):466-71 (1995).
Denham, et al., "Twenty-Four Hour Canine Renal Preservation by Pulsatile Perfusion, Hypothermic Storage, and Combinations of the Two Methods," Transplant Proc. 9(3):1553-56 (1977).
Dobrian, et al., "In vitro formation of oxidatively-modified and reassembled human low-density lipoproteins," Biochimica et Biophysica Acta (BBA) 1169:12-24 (1993).
Drexler et al., "Effect of L-Arginine on Coronary Endothelial Function in Cardiac Transplant Recipients," Circulation. 89(4):1615-23 (1994).
Eiseman, et al., "A Disposable Liver Perfusion Chamber," Surgery 6:1163-66 (1966).
Engelman et al. "Influence of Steroids on Complement and Cytokine Generation After Cardiopulmonary Bypass," Ann. Thorac. Surg. 60(3):801-04 (1995).
Fabregas, Luis, "UPMC Tests Machine to Aid Heart Transplants," Pittsburg Tribune-Review (2002).
Faggian, et al., "Donor Organ Preservation in High-Risk Cardiac Transplantation," Transplant Proc. 36:617-19 (2004).
Fehrenberg, et al., "Protective Effects of B2 Preservation Solution in Comparison to a Standard Solution (Histidine-Tryptophan-Ketoglutarate/Bretschneider) in a Model of Isolated Autologous Hemoperfused Porcine Kidney," Nephron. Physiol. 96:52-58 (2004).
Ferrera et al., "Comparison of Different Techniques of Hypothermic Pig Heart Preservation," Ann. Thorac. Surg. 57(5):1233-39 (1994).
Finn et al., Effects of Inhibition of Complement Activation Using Recombinant Soluble Complement Receptor 1 on Neutrophil CD11B/CD18 and L-Selectin Expression and Release of Interleukin-8 and Elastase in Simulated Cardiopulmonary Bypass. J. Thorac. Cardiovasc. Surg. 111(2):451-49 (1996).
Fourcade, et al., "A New Method of Kidney Preservation with Collins' Solution," Biomed. 21(7):308-11 (1974).
Fraser, et al., "Evaluation of Current Organ Preservation Methods for Heart-Lung Transplantation," Transplant. Proc. 20(1 Suppl. 1):987-90 (1988).
Guarrera, et al., "Pulsatile Machine Perfusion with Vasosol Solution Improves Early Graft Function After Cadaveric Renal Transplantation," Transplantation 77(8):1264-68 (2004).
Gundry et al., "Successful Transplantation of Hearts Harvested 30 Minutes After Death From Exsanguination," Ann. Thorac. Surg. 53(5):772-75 (1992).
Habazetti et al., "Improvement in Functional Recovery of the Isolated Guinea Pig Heart After Hyperkalemic Reperfusion with Adenosine," J. Thorac. Cardiovasc. Surg. 111(1):74-84 (1996).
Hachida, et al., Abstract "Efficacy of Myocardial Preservation using HTK Solution in Continuous 120 Min. Cross-Clamping Method—a Comparative Study with GIK Method," Nippon Kyobu Geka Gakkai Zasshi 41(9):1495-1501 (1993).

Hartman, J.C. "The Role of Bradykinin and Nitric Oxide in the Cardioprotective Action of ACE Inhibitors," Ann Thor. Surg. 60:789-92 (1995).
Hassanein, et al., "A Novel Approach for 12-Hour Donor Heart Preservation, Presented at the 70th Scientific Session of the American Heart Association," Abstract was published in Circulation (1977).
Hassanein, et al., "Continuous Perfusion of Donor Hearts in the Beating State Extends Preservation Time and Improves Recovery of Function," The Journal of Thoracic and Cardiovascular Surgery, pp. 821-830 (1988).
"Heart Kept Beating Outside Body," Associated Press, CNN.com (2001).
Heil, et al., "A Controlled Comparison of Kidney Preservation by Two Methods: Machine Perfusion and Cold Storage," Transplant. Proc. 19(1):2046 (1987).
History of Transplantation and Organ Preservation, Barr Laboratories,Inc. (internet reference) (2004).
"Human Heart Beats on its own Outside Body," USA Today (2001).
"Human Heart Kept Alive Outside Body for First Time in Study of Portable Organ Preservation System™ at University of Pittsburgh Medical Center," UPMC, McGowan Institute for Regenerative Medicine (2001).
Imber, et al., "Advantages of Normothermic Perfusion Over Cold Storage in Liver Preservation," Transplantation, 73(5):701-09 (2002).
Janssen, et al., "UW is Superior to Celsior and HTK in the Protection of Human Liver Endothelial Cells Against Preservation Injury," Liver Transpl., 10(12):1514-23 (2004).
Kawamura, et al., "Long-Term Preservation of Canine Pancreas by a New Simple Cold Storage Method Using Perfluorochemical—The Two-Layer Cold Storage Method (Euro-Collins' Solution/Perfluorochemical)," Kobe J. Med. Sci., 38(2):135-45 (1992).
Kelly, "Current Strategies in Lung Preservation," J. Lab Clin. Med., 136:427-40 (2000).
Keshavjee, et al., "A Method for Safe Twelve-Hour Pulmonary Preservation," J. Thorac. Cardiovasc Surg., 98:529-34 (1989).
Kioka, et al., "Twenty-Four-Hour Isolated Heart Preservation by Perfusion Method With Oxygenated Solution Containing Perfluorochemicals and Albumin," J. Heart Transplant., 5:437-43 (1986).
Kozaki, et al., "Usefulness of a Combination of Machine Perfusion and Pentoxifylline for Porcine Liver Transplantation From Non-Heart-Beating Donors With Prolonged Hypotension," Transplant Proc., 29:3476-77 (1997).
Kuroda, et al., "A New, Simple Method for Cold Storage of the Pancreas Using Perfluorochemical," Transplantation, 46(3):457-60 (1988).
Lasley, et al., "Protective Effects of Adenosine in the Reversibly Injured Heart," Ann. Thorac. Surg., 60(3):843-46 (1995).
Lawrence, "Machine Preserves Organs Outside Body," Chicago Sun Times (2001).
Lefer, A.M., "Attenuation of Myocardial Ischemia-Reperfusion Injury With Nitric Oxide Replacement Therapy." Ann. Thorac. Surg. 60(3):847-51 (1995).
Li, et al., "Insulin in University of Wisconsin Solution Exacerbates the Ischemic Injury and Decreases the Graft Survival Rate in Rat Liver Transplantation," Transplantation, 15:76(1):44-49 (2003).
Li, et al., "Insulin in UW Solution Exacerbates Hepatic Ischemia/Reperfusion Injury by Energy Depletion Through the IRS-2/SREBP-1C Pathway," Liver Transp., 10(9):1173-82 (2004).
Li, G. et al., "Functional Recovery in Rabbit Heart after Preservation with a Blood Cardioplegic Solution and Perfusion," J. Herat Lung Transplant. 12(2)263-70 (1993).
Liu, et al., "Annexin V Assay-proven Anti-apopotic Effect of Ascorbic Acid 2-glucoside after Cold Ischemia/Reperfusion Injury in Rat Liver Transplantation," Acta Med. Okayama, 57(5):209-16 (2003).
"Machine Keeps Human Kidney Alive for 24-Hours," 222. worldhealth.net, Aug. 25, 2001.
"Machine May Be Organ Transplant Breakthrough," USA Today (2001).

(56) References Cited

OTHER PUBLICATIONS

Mankad et al., "Endothelial dysfunction caused by University of Wisconsin preservation solution in the rat heart," J. Thorac. Cardiovasc. Surg. 104(6): 1618-24 (1992).
Matsuno et al., "Effectiveness of Machine Perfusion Preservation as a Viability Determination Method for Kidneys Procured from Non-Heart-Beating Donors," Transplant. Proc. 26(4):2421-22 (1994).
Matsuno et al., "The Effect of Machine Perfusion Preservation Versus Cold Storage on the Function of Kidneys from Non-Heart-Beating Donors," Transplantation. 57(2):293-94 (1994).
Menasche et al., "Experimental evaluation of Celsior®. a new heart preservation solution," Eur. J. Cardiothor. Surg. 8:207-13 (1994).
Menasche, et al., "Improved Recovery of Heart Transplants With a Specific Kit of Preservation Solutions," J. Thorac. Cardiovasc. Surg., 105(2):353-63 (1993).
Menasche, P., "The inflammatory response to cardiopulmonary bypass and its impact on postoperative myocardial function", Curr. Opin. Cardiology. 10:597-604 (1995).
Moisiuk, et al., "Histidine-Tryptophan-Ketoglutarate Versus Euro-Collins for Preservation of Kidneys from Non-Heart-Beating Donors," Transplant Proc., 28(1):202 (1996).
Moller-Pedersen, et al., "Evaluation of Potential Organ Culture Media for Eye Banking Using Human Donor Corneas," Br. J. Ophthamol, 85(9):1075-79 (2001).
Morimoto, et al., "A Simple Method for Extended Heart-Lung Preservation by Autoperfusion," Trans. Am. Soc. Artif Intern Organs., 30:320-24 (1984).
"New Discovery in Organ Transplantation," MSNBC (2001).
Innovations—Report "New Organ Preservation Solution Easier to Use," (internet reference) (2003).
Nicholson, et al., "A Comparison of Renal Preservation by Cold Storage and Machine Perfusion Using a Procine Autotransplant Model," Transplantation 78(3):333-37 (2004).
Opelz, et al., "Advantage of Cold Storage Over Machine Perfusion for Preservation of Cadaver Kidneys," Transplantation, 33(1):64-68 (1982).
Opelz, et al., "Comparative Analysis of Kidney Preservation Methods, Collaborative Transplant Study," Transplant Proc. 28(1):87-90 (1996).
Pearl et al., "Loss of endothelium-dependent vasodilation and nitric oxide release after myocardial protection with University of Wisconnsin solution," J. Thorac. Cardiovasc. Surg., 107(1):257-64 (1994).
Petrovsky, et al., Justification and Application of a New Method for Transorganic Oxygen Preservation of the Kidneys, Vestn. Akad. Med. Nauk, SSSR., (2):69-82 (1989).
Pinsky et al., "Restoration of the cAMP Second Messenger Pathway Enhances Cardiac Preservation for Transplantation in a Heterotopic Rat Model," J. Clin. Invest. 92(6):2944-3002 (1993).
Ploeg, et al., "Successful 72-Hour Cold Storage of Dog Kidneys with UW Solution," Transplantation, 46(2):191-96 (1988).
Pokorny, et al., "Histidine-Tryptophan-Ketoglutarate Solution for Organ Preservation in Human Liver Transplantation—A Prospective Multi-Centre Observation Study," Transpl. Int. 17(5):256-60 (2004).
Potdar, et al., "Initial Experience Using Histidine-Tryptophan-Ketoglutarate Solution in Clinical Pancreas Transplantation," Clin. Transplant., 18(6):661-65 (2004).
Pozniak, "Keeping Hearts Alive: Doctors Develop a High-Tech System to Salvage Donated Organs," ABC News.com (2001).
Rao et al., "Donor blood Perfusion Improves Myocardial Recovery After Heart Transplantaion," J. Heart Lung Transplant, 16(6):667-73 (1997).
Reddy, et al., "Preservation of Porcine Non-Heart Beating Donor Livers by Sequential Cold Storage and Warm Perfusion," Transplantation, 77(9):1328-32 (2004).
Richens et al., "Clinical Study of Crystalloid Cardioplegia vs Aspartate-Enriched Cardioplegia Plus Warm Reperfusion for Donor Heart Preservation," Transplant. Proc. 24(1): 1608-10 (1993).
Rinder et al., "Blockade of C5a and C5b-9 Generation Inhibits Leukocyte and Platelet Activation during Extracorporeal Circulation," J. Clin. Invest. 96:3(1564-72). 1995.
Rossi, "Portable Organ Preservation System™ Keeps Human Heart Alive Outside Body," PITT Campaign Chronicle (2001).
Rosenkranz, E.R. "Substrate Enhancement of Cardioplegic Solution: Experimental Studies and Clinical Evaluation," Ann. Thorac. Surg. 60:797-800 (1995).
Sato, H. et al., "Supplemental L-Arginine During Cardioplegic Arrest and Reperfusion Avoids Regional Postischemic Injury," J. Thorac. Cardiovasc. Surg. 110(2):302-14 (1995).
Schmid, et al., "The Use of Myocytes as a Model for Developing Successful Heart Preservation Solutions," Transplantation, 52(1):20-6 (Jul. 1991).
Schon, et al., "Liver Transplantation After Organ Preservation by Normothermic Extracorporeal Perfusion," Ann. Surg. 233(1):114-23 (2001).
Schwalb et al., "New Solution for Prolonged Myocardial Preservation for Transplantation," J. Heart Lung Transplant. 17(2):222-29 (1998).
Seccombe et al., "Coronary Artery Endothelial Function After Myocardial Ischemia and Reperfusion," Ann. Thorac. Surg. 60(3):778-88 (1995).
Segel et al., "Posttransplantation Function of Hearts Preserved with Fluorochemical Emulsion", J. Heart Lung Transplant. 13(4):669-80 (1994).
Segel, et al., "Recovery of Sheep Hearts After Perfusion Preservation or Static Storage With Crystalloid Media," The Journal of Heart and Lung Transplantation, 17:211-21 (1998).
Shimokawa, et al., "A New Lung Preservation Method of Topical Cooling by Ambient Cold Air Combined with High-Frequency Oscillation: An Experimental Study," Transplant. Proc., 26(4):2364-66 (1994).
Shimokawa, et al., "A New Lung Preservation Method of Topical Cooling by Ambient Cold Air: An Experimental Study," Transplant. Proc., 23 (1 Pt 1):653-54 (1991).
Shirakura et al., "Multiorgan Procurement from Non-Heart-Beating Donors by use of Osaka University Cocktail, Osaka Rinse Solution, and the Portable Cardiopulmonary Bypasss Machine," Transplant. Proc. 25(6):3093-94 (1993).
Southard, "The Right Solution for Organ Preservation", Business Briefings: Global Surgery, 79-84 (2004).
Stubenitsky, et al., "Kidney Preservation in the Next Millenium," Transpl. Int., 12:83-91 (1999).
Sunamori et al., "Relative Advantages of Nondepolarizing Solution to Depolarizing University of Wisconsin Solution in Donor Heart Preservation," Transplant. Proc. 25(1): 1613-17 (1993).
Tang, et al., "Warm Ischemia Lung Protection with Pinacidil: An ATP Regulated Potassium Channel Opener," Ann. Thorac. Surg., 76:385-9 (2003).
Tesi et al., "Pulsatile Kidney Perfusion for Preservation and Evaluation: Use of High-Risk Kidney Donors to Expand the Donor Pool," Transplant. Proc. 25(6):3099-100 (1993).
The Merck Index, 11th ed. Entry 4353 (pp. 699-700) (1989).
"The Nation Warm-Storage Device May Aid Organ Transplants," Dow Jones Publications Library (2001).
Turpin, et al., "Perfusion of Isolated Rat Adipose Cells," The Journal of Clinical Investigation, 60:442-448 (1977).
"ViaSpan (Belzer UW) Cold Storage Solution," Barr Laboratories, Inc. (2002).
Vinten-Johansen, et al., "Reduction in Surgical Ischemic-Reperfusion Injury With Adenosine and Nitric Oxide Therapy," Ann. Thorac. Surg. 60(3):852-57 (1995).
"Warm-Storage for Donor Organs," Univ. of Chicago Magazine (2001).
Watanabe, et al., "Effects of free fatty acids on the binding of bovine and human serum albumin with steroid hormones," Biochimica et Biophysica Acta (BGBA), 1289:385-96 (1996).
Wicomb et al., "24-Hour Rabbit Heart Storage with UW Solution," Transplantation. 48(1):6-9 (1989).
Wicomb, et al., "Cardiac Transplantation Following Storage of the Donor Heart by a Portable Hypothermic Perfusion System," The Annals of Thoracic Surgery, 37(3):243-48 (1984).

(56) References Cited

OTHER PUBLICATIONS

Wicomb, et al., "Orthotopic Transplantation of the Baboon Heart After 20 to 24 Hours Preservation by Continuous Hypothermic Perfusion With an Oxygenated Hyperosmolar Solution," The Journal of Thoracic and Cardiovascular Surgery, 83(1):133-40 (1982).
Yland, et al., "New Pulsatile Perfusion Method for Non-Heart-Beating Cadaveric Donor Organs: A Preliminary Report," Transplantation Proceedings, 25(6):3087-90 (1993).
Zhang, et al., "Research Progress on Preservation of Severed Limbs," Chinese Journal of Reparative and Reconstructive Surgery, 14(3):189-192 (2000).
Zhengquang, et al., "A Study on the Preservation of Rat Kidney with HX-III Solution," WCUMS, 31(3):347-49 (2000).
Barinov, et al. "Hormonal-metabolic disturbances during biological preservation of the heart," Fiziol. ZH., (Kiev), 29(3):293-299 (1983) (7 pages)—Russian Language.
Brandes, H et al. "Influence of high molecular dextrans on lung function in an ex vivo porcine lung model." J. of Surgical Research. 101:2 225-231. Dec. 2001, 7 pages.
European Search Report for European Patent Application No. 08795820.3 mailed Apr. 17, 2014. 6 pages.
European Search Report for European Patent Application No. 09707471.0 mailed May 27, 2014. 7 pages.
Featherstone et al. "Comparison of Phosphodiesterase Inhibitors of Differing Isoenzyme Selectivity Added to St. Thomas' Hospital Cardioplegic Solution Used for Hypothermic Preservation of Rat Lungs." Am. J. Respir. Crit. Care Med. Mar. 2000. 162(3):850-856, 7 pages.
File History for U.S. Appl. No. 60/616,835, filed Oct. 7, 2004. 82 pages.
File History for U.S. Appl. No. 60/694,971, filed Jun. 28, 2005. 280 pages.
File History for U.S. Appl. No. 60/725,168, filed Oct. 6, 2005. 699 pages.
Grynberg et al. "Fatty acid oxidation in the heart," Journal of Cardiovascular Pharmacology, 28(Suppl. 1):S11-S17 (No Month Given1996) (8 pages).
Hardesty et al. Original Communications, "Autoperfusion of the heart and lungs for preservation during distant procurement," J. Thorac. Cardiovasc. Surg., 93:11-18 (No Month Given 1987) (8 pages).
Hülsmann et al. "Loss of cardiac contractility and severe morphologic changes by acutely lowering the pH of the perfusion medium: protection by fatty acids," BBAGEN 20256, Biochimica et Biophysica Acta., 1033:214-218 (Feb. 26, 1990) (5 pages).
International Search Report and Written Opinion for International Application No. PCT/US12/33626 mailed Sep. 20, 2012. 12 pages.
International Search Report for PCT/US07/009652 mailed Apr. 18, 2008, 7 pages.
Johnson, Kerry et al: "POPS: Portable Organ Preservation System." UPMC Health System and TransMedics, Inc. Tribune Review (No date) 1 page.
Katz, Robert et al. "Physics, Chapter 9: Hydrodynamics (Fluids in Motion)." Hydrodynamics. University of Nebraska—Lincoln. Paper143. No Month Listed 1958. 18 pages.
Macchiarini et al. "Ex vivo lung model of pig-to-human hyperacute xenograft rejection," J. of Thoracic and Cardiovascular Surgery, 114:3, 315-325 (Sep. 1997) (9 pages).
No Author Listed. "Custodiol HTK Solution for Multi-Organ Protection." Saudi Center for Organ Transplantation. Date Unknown. 2 pages.
No Author Listed. "Custodiol HTK." Physicians' Desk Reference. 57th Edition, Thomson PDR. ISBN:1-56363-445-7. No Month Listed—2003. 3 pages.
No Author Listed. "Soltran Kidney Perfusion Fluid." Baxter. No Month Listed—2001-2004. 1 page.
No Author Listed. "The Comprehensive Resource for Physicians, Drug and Illness Information." Viaspan DuPont Pharma Cold Storage Solution. Date Unknown. 3 pages.
No Author Listed. "UW Solution Composition." Date Unknown. 1 page.
PCT/US08/61454 International search report mailed Dec. 5, 2008 (3 pages).
PCT/US09/032619 International search report mailed Jun. 4, 2009 (4 pages).
PCT/US98/19912 International search report mailed May 3, 1999 (4 pages).
Probst et al. "Carbohydrate and fatty acid metabolism of cultured adult cardiac myocytes," Am. J. Physiol. 250 (Heart, Circ. Physiol. 19):H853-H860 (1986) (8 pages).
"Celsior, Cold Storage Solution." Sangstat Medical Corporation and Fresenius Kabi France. (No date), 5 pages.
Solu-Medrol, Drug Details, U.S. Food and Drug Administration, Center for Drug Evaluation and Research, "Drugs@FDA—Drug Details" (Accessible online at http://www.accessdata.fda.gov/scripts/cder/drugsatfda/index.cfm?fuseaction=Search.DrugDetails) (1 page).
Solu-Medrol, Label and Approval History U.S. Food and Drug Administration, Center for Drug Evaluation and Research, "Drugs@FDA—Label and Approval History," (Available online at http://www.accessdata.fda.gov/scripts/cder/drugsatfda/index.cfm?fuseaction=Search.Label_ApprovalHistory#apphist) (3 pages).
Voiglio et al. "Rat multiple organ blocks: microsurgical technique of removal for ex vivo aerobic organ preservation using a fluorocarbon emulsion," Microsurgery 20: 109-115 (No Month Given 2000), 7 pages.
Wright, N. et al. "A porcine ex vivo paracorporeal model of lung transplantation." Laboratory Animals. 34:1 56-62 (No Month Given 2000), 7 Pages.
Aitchison, J. Douglas et al. "Nitric Oxide During Perfusion Improves Posttransplantation Function of Non-Heart-Beating Donor Lungs." Transplantation. Jun. 27, 2003. vol. 75, No. 12, pp. 1960-1964.
European Search Report for European Patent Application No. 12770852.7 mailed Sep. 23, 2014. 8 pages.
Odagiri, Shigetoh et al. "New Pulsatile Pump Using Pulsatile Assist Device—Hemodynamic Comparison of Pulsatile V-A Bypass (VABP), Pulsatile Left Heart ByPass (LHBP) and Constant Flow Left Heart Bypass (LHB)." Journal of Japan Surgical Society. V83, No Month Listed 1983. pp. 515-523, 12 pages.
Ota et al. "Artificial Organ—Current State and Future of Substitution of Functions." No Month Listed 1983. pages 150-151, 4 pages.
Steen, Stig et al. "Transplantation of Lungs from Non-Heart-Beating Donors After Functional Assessment Ex Vivo." The Annals of Thoracic Surgery. Elsevier Inc. No Month Listed 2003. vol. 76, pp. 244-252.
Carrier, B. et al., "Chapter 4: Hypoxia and Oxygenation", Alaska Air Medical Escort Training Manual, Fourth Edition, pp. 71-82, 2006 (12 pages).
Definition of Synchrony, http://dictionary.reference.com/browse/synchrony. Random House Unabridged Dictionary, 2006 (1 page).
Egan, T. M. et al., "Ex Vivo Evaluation of Human Lungs for Transplant Suitability", Ann Thorac Surg, vol. 81, No. 4, pp. 1205-1213 (Apr. 2006) (9 pages).
Howarth, F.C. et al., "Effects of extracellular magnesium and beta adrenergic stimulation on contractile force and magnesium mobilization in the Isolated rat heart", Magnesium Research, 7:187-197, 1994 (13 pages).
Poston, R.S. et al., "Optimizing Donor Herat Outcome After Prolonged Storage With Endothelial Function Analysis and Continuous Perfusion", Ann Thorac Surg, 78:1362-1370, 2004 (9 pages).

* cited by examiner

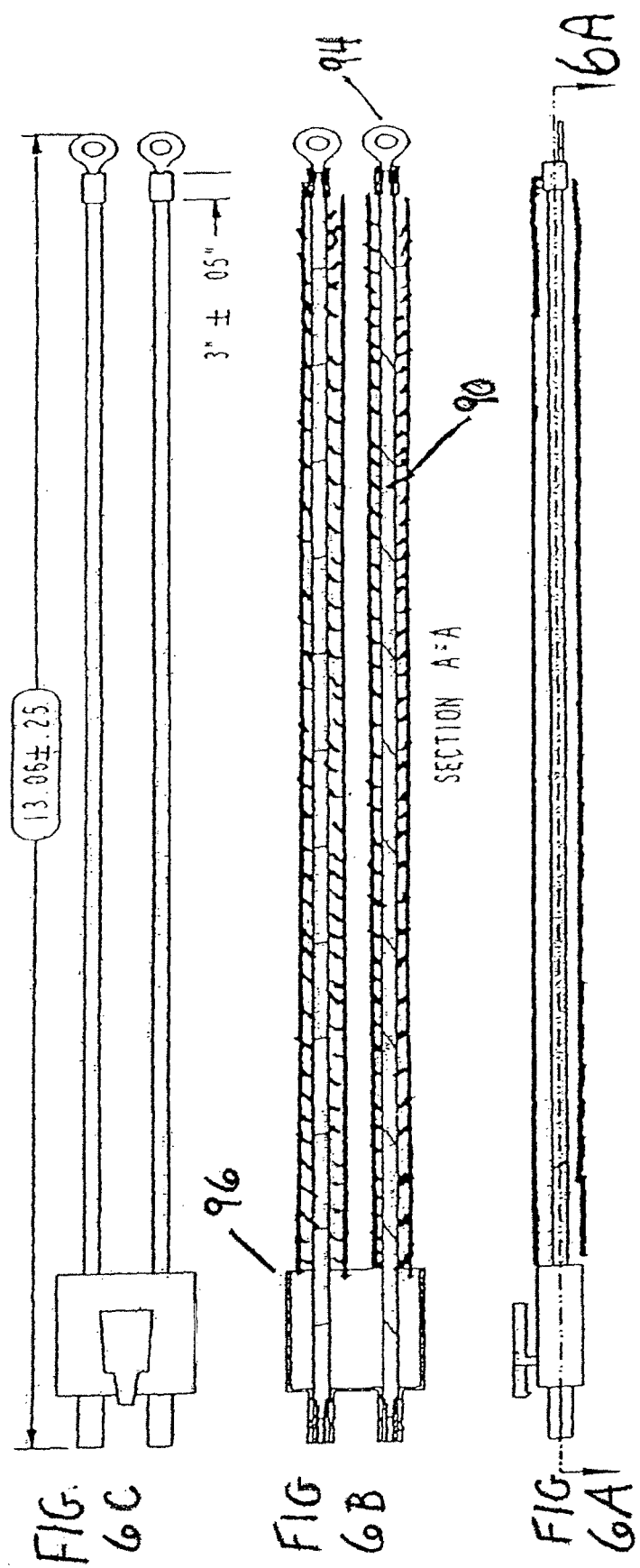

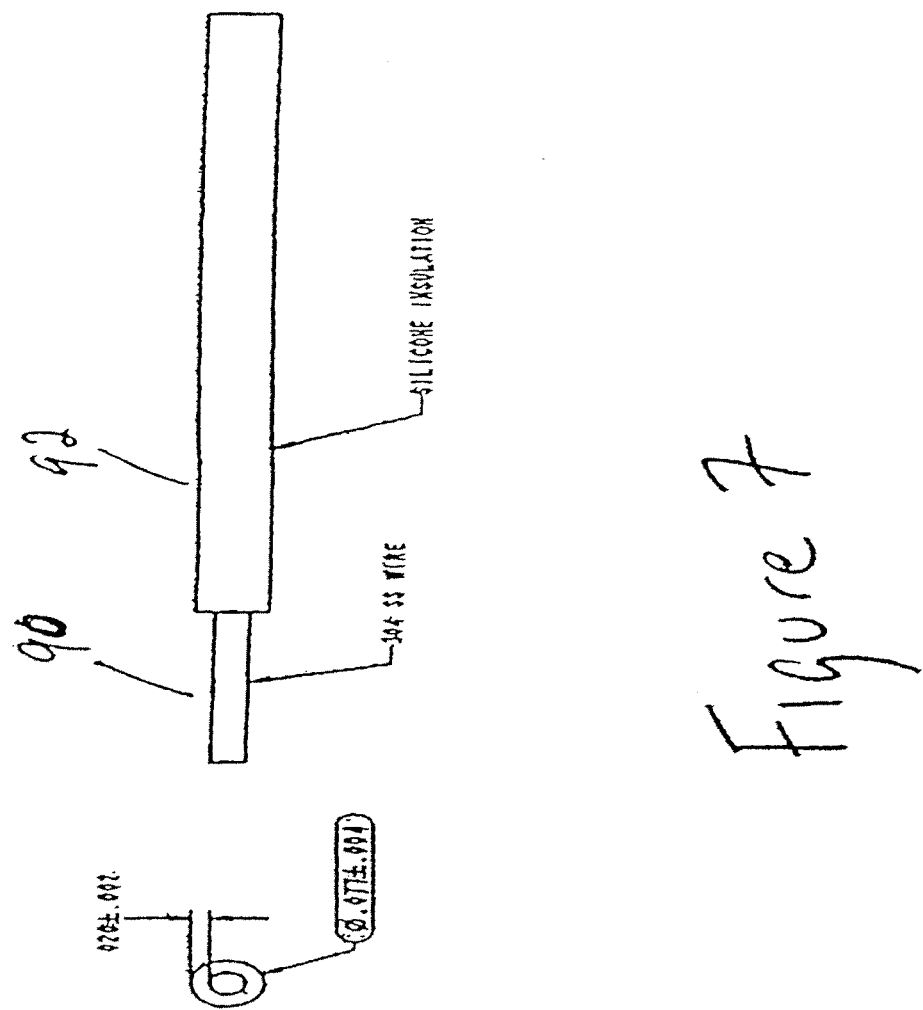

SYSTEMS FOR MONITORING AND APPLYING ELECTRICAL CURRENTS IN AN ORGAN PERFUSION SYSTEM

RELATED APPLICATIONS

This application is related to Application Ser. No. 60/919,306, titled "Systems for Monitoring Organ Electrical Activity in a Perfusion System," filed Mar. 20, 2007, which is incorporated herein by reference in its entirety.

BACKGROUND OF THE INVENTION

Organ preservation techniques typically involve hypothermic storage of the organ in a chemical perfusate solution on ice. In the case of a heart, it is typically arrested, and cooled with a cardioplegic solution until it reaches a hypothermic, non-functioning state and then is stored in or perfused with a cold preservation solution. These techniques utilize a variety of cardioplegic and cold preservation solutions, none of which sufficiently protect the heart from myocardial damage resulting from ischemia. Such injuries are particularly undesirable when an organ, such as a heart, is intended to be transplanted from a donor into a recipient. In addition to myocardial damage resulting from ischemia, reperfusion of a heart may exacerbate the myocardial injury and may cause coronary vascular endothelial and smooth muscle injury, which may lead to coronary vasomotor dysfunction.

Using conventional approaches, such injuries increase as a function of the length of time an organ is maintained ex-vivo. For example, in the case of a heart, typically it may be maintained ex-vivo for only 4-6 hours before it becomes unusable for transplantation. This relatively brief time period limits the number of recipients who can be reached from a given donor site, thereby restricting the recipient pool for a harvested heart. Even within the 4-6 hour time limit, the heart may nevertheless be significantly damaged. A significant issue is that there may not be any apparent indication of the damage. Compounding the effects of cold ischemia, current cold preservation techniques preclude the ability to evaluate and assess an organ ex-vivo. Because of this, less-than-optimal organs may be transplanted, resulting in post-transplant organ dysfunction or other injuries. Thus, it would be desirable to develop techniques that can extend the time during which an organ can be preserved in a healthy state ex-vivo and that can provide an environment within which an organ can be evaluated ex-vivo. Such techniques would improve transplant outcomes and enlarge potential donor and recipient pools.

Effective maintenance of an ex-vivo organ would also provide numerous other benefits. For instance, ex-vivo maintenance of an organ in a living, functioning, near-physiologic state would permit more careful monitoring and evaluation of the harvested organ. This would in turn allow earlier detection and potential repair of defects in the harvested organ, further improving transplant at outcomes. The ability to perform simple repairs on the organ would also allow many organs with minor defects to be saved, whereas current transplantation techniques require them to be discarded.

In addition, more effective matching between the organ and a particular recipient may be achieved, further reducing the likelihood of eventual organ rejection. Current transplantation techniques rely mainly on matching donor and recipient blood types, which by itself is not a foolproof indicator of whether or not the organ will be rejected by the recipient. A more complete test for organ compatibility is a Human Leukocyte Antigen (HLA) matching test, but current cold ischemic organ preservation approaches preclude the use of this test, which can often require twelve hours or more to complete.

Prolonged and reliable ex-vivo organ care would also provide benefits outside the context of organ transplantation. For example, a patient's body, as a whole, can typically tolerate much lower levels of chemo-, bio- and radiation therapy than many particular organs. An ex-vivo organ care system would permit an organ to be removed from the body and treated in isolation, reducing the risk of damage to other parts of the body.

Electrodes are used in some heart perfusion systems to measure the electrical activity of the explanted heart and to deliver defibrillation energy. There are a number of issues associated with these electrodes, such as their size, which makes them difficult to position and may cause them to come in contact with each other resulting in erroneous signals, particularly on smaller hearts. In addition, these electrodes require wetting with blood to establish electrical contact with the heart, have a tendency to move around due to vibration during transport and beating of the heart resulting in a loss of signal fidelity, have biocompatibility issues, and are incompatible with the sterilization method (ETO) used to sterilize components of the perfusion systems.

SUMMARY OF EMBODIMENTS OF THE INVENTION

Electrode systems have been developed for use in perfusion systems to measure the electrical activity of an explanted heart and to provide defibrillation energy as necessary. The perfusion systems maintain the heart in a beating state at, or near, normal physiologic conditions; circulating oxygenated, nutrient enriched perfusion fluid to the heart at or near physiologic temperature, pressure and flow rate. These systems include a pair of electrodes that are placed epicardially on the right atrium and left ventricle of the explanted heart, as well as an electrode placed in the aortic blood path.

An advantage of this configuration allows an electrode to be held against the right atrium of the explanted heart under the heart's own weight, which reduces the likelihood that the electrode will shift during transport of the heart due to vibrations or the beating of the heart itself. As well, placing the electrode epicardially allows the electrode to be manipulated to ensure better electrical connection as well as adjustments for differently shaped and sized hearts.

Further, placement of an electrode in the aortic bloodpath supplies a more stable position for the sensing and detection of electrocardiogram (ECG) signals from the heart. This configuration provides an electrical connection for sensing and detecting ECG signals from the electrode in the aortic bloodpath, through the blood and heart muscle to the electrode, placed epicardially, on the right atrium. This electrode configuration has been shown to provide more stable ECG signals than two electrodes placed epicardially on the heart.

In addition to sensing and detecting ECG signals, the right atrial electrode, in combination with a left ventricle electrode, is used to deliver defibrillation energy and/or pacing signals to the explanted heart after being placed in a perfusion system to ensure the heart is beating normally before the organ chamber is sealed. After the heart is beating normally, the left ventricle electrode may be moved aside, such that fewer elements are in contact with the heart that may cause irritation to the tissue. However, it is envisioned that in some embodiments, the left ventricle electrode may be left in place after a normal heart beat is achieved so defibrillation energy and/or pacing signals may be delivered to the heart after the organ chamber is sealed without the need for further manipulating the electrode through the membrane.

A perfusion system for maintaining an organ ex-vivo may include a housing comprising an outer lid and an intermediate lid. The intermediate lid covers an opening to the housing for substantially enclosing the organ within the housing, and includes a frame and a flexible membrane suspended within the frame. The flexible membrane includes sufficient excess membrane material to contact an organ contained within the chamber, which enables a medical operator to touch/examine the organ indirectly through the membrane or manipulate one or more electrodes contained within the organ chamber while still maintaining sterility of the system and the organ. The outer lid opens and closes over the intermediate lid independently from the intermediate lid. Preferably, the outer lid is rigid enough to protect the organ from physical contact, indirect or direct, and provide structural integrity to the organ chamber assembly.

The organ chamber assembly includes a pad or a sac assembly sized and shaped for interfitting within a bottom of the housing. Preferably, the pad assembly includes a pad formed from a material resilient enough to cushion the organ from mechanical vibrations and shocks during transport. In a preferred embodiment, the pad assembly is formed from silicone, which is biocompatible, impervious to liquids, capable of surviving sterilization processes (ETO, etc.) and provides a non-slip surface for electrodes. According to one embodiment, the pad of the invention includes a mechanism for receiving at least one electrode. The mechanism allows for adjustable placement of the at least one electrode on or in the pad to accommodate differently sized and shaped hearts. The pad may include a through-aperture through which an electrical lead of the at least one electrode may pass. The sac assembly may be two or more layers of silicone film sealed together and filled with air or fluid.

In all embodiments of the present invention, all blood and tissue contacting materials have been selected for their high degree of biocompatibility.

BRIEF DESCRIPTION OF THE DRAWINGS

FIG. 6a-c illustrate an embodiment of a cable assembly for use with the electrodes of a system for delivering electrical energy to an organ;

FIG. 7 illustrates an embodiment of a specially designed wire for use with the electrodes of a system for monitoring organ electrical activity;

DETAILED DESCRIPTION OF THE INVENTION

Three electrodes are provided such that various connections may be made to a system for monitoring organ electrical activity in a perfusion system and providing, when appropriate, electrical energy to the organ. Two electrodes are placed proximate an explanted heart, preferably within a sterile environment. A third electrode is placed in the flow of the aortic perfusion fluid. This configuration allows for the monitoring of ECG signals of the explanted heart as well as for the delivery of defibrillation energy and/or pacing signals to the heart.

Electrodes for epicardial placement are constructed of 304 stainless steel and are partially covered with silicone, which provides electrical insulation, is impervious to fluids, is biocompatible and provides a non-slip surface to aid in maintaining placement of the electrodes. The metal surface of the stainless steel electrodes is passivated to improve electrical performance, provide corrosion resistance and enhance biocompatibility. Electrodes for epicardial placement are resistance welded to 304 stainless steel wire contained within silicone insulation. The silicone wire insulation and silicone electrode covering are joined to provide protection for the weld as well as flexibility in the wire. The electrode placed in the flow of the aortic perfusion fluid is a thermal well constructed of 304 stainless steel and polycarbonate, into which has been potted a gold plated pin using electrically conductive epoxy. In certain embodiments, at least a portion of the electrode placed in the flow of the aortic perfusion fluid is covered with silicone to improved biocompatibility.

Placement of one electrode in the flow of the aortic perfusion fluid allows for more stable ECG readings as the electrode is less susceptible to vibrations during transport as well as movement from a beating heart. After a normal heart beat is achieved, one electrode for epicardial placement may be removed or moved aside, which may reduce any potential irritation of the heart tissue, provide fewer opportunities for the electrodes to touch, as well as provide more maneuverability of the remaining electrode for obtaining better placement on the heart. After placement, the electrodes for epicardial placement are maintained in position, at least partially, by the weight of the explanted heart.

In operation, a completed electrical circuit for measuring ECG signals from the explanted heart exists from the electrode in the flow of the aortic perfusion fluid to an electrode for epicardial placement on the heart through the perfusion fluid and heart muscle. Defibrillation energy and/or pacing signals may be provided to the explanted heart by the electrodes for

EXAMPLES OF CERTAIN EMBODIMENTS

Figure 1:
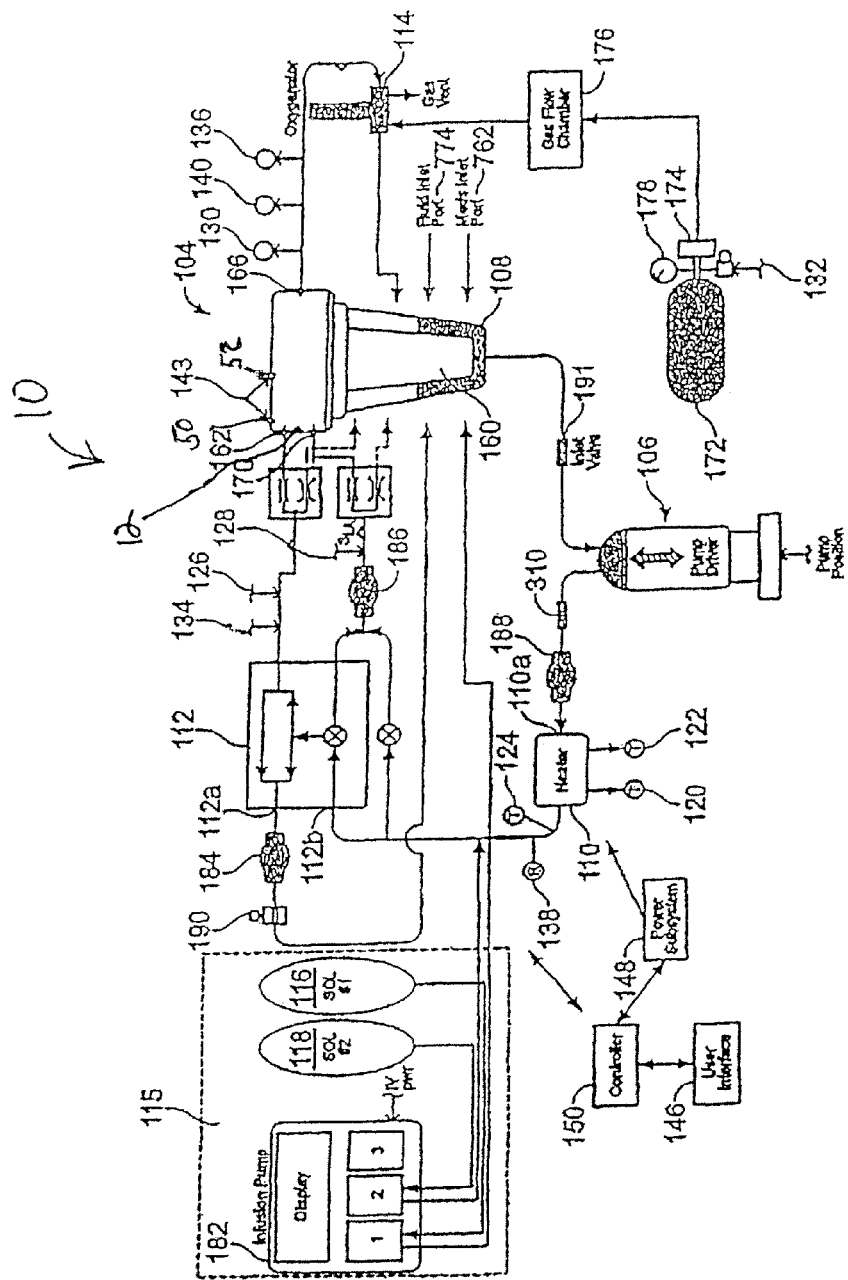
FIG. 1 illustrates a schematic diagram of a portable organ care system.

Illustrative apparatuses, systems and methods of perfusing an organ that may be adapted to incorporate the electrode systems of the present invention are described in co-pending application Ser. No. 11/246,902, titled "Systems and Methods for Ex-Vivo Organ Care," filed Oct. 5, 2005, which is incorporated herein by reference in its entirety, an example of which is shown in FIG. 1. Any operative combinations between any of the features, advantages, systems or methods described in any of the figures or applications upon which priority has been claimed or that have been incorporated by reference are considered part of the patentable subject matter contained herein.

Referring to FIG. 1, an embodiment of a perfusion system 10 is depicted, which includes an organ chamber assembly 104 for containing the heart 102 (not shown) during ex-vivo maintenance, a reservoir 160 for holding, defoaming and filtering the perfusion fluid 108, portal 774 for loading perfusion fluid 108 into the reservoir 160 and a portal 762 for applying therapeutics to the fluid 108 contained in the reservoir 160, a perfusion fluid pump 106 for pumping/circulating perfusion fluid 108 to and from the harvested heart 102; a heater assembly 110 for maintaining the temperature of the perfusion fluid 108 at or near physiologic temperatures; a flow mode selector valve 112 for switching between normal and retrograde aortic flow modes (also referred to as "normal flow mode" and "retrograde flow mode," respectively); an oxygenator 114 for oxygenating the perfusion fluid 108 subsequent to it being deoxygenated by the heart 102 from aerobic respiration; a nutritional subsystem 115 containing an infusion pump 182 for replenishing energy substrates 116 in the perfusion fluid 108 as they are metabolized by the heart 102 and for providing additional nutrients and amino acids 118 to the perfusion fluid to reduce, for example, re-perfusion related injuries to the heart 102. An inlet valve 191 and the reservoir 160 are oriented to provide a gravity feed of perfusion fluid 108 into the pump assembly 106.

The illustrative perfusion system 10 also includes a plurality of sensors, including without limitation: temperature sensors 120, 122 and 124; pressure sensors 126, 128, 130 and 132; perfusion flow rate sensors 134, 136 and 138; a perfusion fluid oxygenation and hematocrit sensor 140; and sensor/defib electrodes 12, 50 and 52, and defibrillation source 143.

The system 10 further includes: various components employed for maintaining suitable flow conditions to and from the heart 102; an operator interface 146 for assisting an operator in monitoring operation of the system 10, and the condition of the heart 102, and for enabling the operator to select various operating parameters; a power subsystem 148 for providing fault tolerant power to the system 10; and a controller 150 for controlling operation of the organ care system 10.

With continued reference to FIG. 1, in both flow modes the perfusion fluid 108 flows from the pulmonary artery interface 166 into the oxygenator 114. The oxygenator 114 receives gas from an external or onboard source 172 through a gas regulator 174 and a gas flow chamber 176, which can be a pulse-width modulated solenoid valve that controls gas flow, or any other gas control device that allows for precise control of gas flow rate. A gas pressure gauge 178 provides a visual indication of amount remaining in the gas supply 172. The transducer 132 provides similar information to the controller 150. The controller 150 can regulate automatically the gas flow into the oxygenator 114 in dependence, for example, on the perfusion fluid oxygen content measured at the sensor 140. Subsequent to oxygenation, the oxygenator 114 returns the perfusion fluid 108 to the reservoir 160. In normal flow mode, the pulmonary vein interface 170 returns oxygenated blood to the left atrium of the heart 102. Blood leaves the left ventricle and enters the aorta interface 162. In retrograde flow mode, the aortic interface delivers oxygenated blood to the coronary arteries via the aorta. After the heart 102 is instrumented onto the system 100, the pump 104 is activated and the flow mode valve 112 is positioned in retrograde flow mode to pump the perfusion fluid 108 in retrograde flow mode through the aorta into the vasculature of the heart 102. The pumping of the warm, oxygen and nutrient enriched perfusion fluid 108 through the heart 102 allows the heart 102 to function ex vivo in a near normal physiologic state. In particular, the warm perfusion fluid 108 warms the heart 102 as it perfuses through it, which may cause the heart 102 to resume beating in its natural fashion.

As shown in FIG. 1, the system 10 also includes a plurality of compliance chambers 184, 186 and 188. The compliance chambers 184, 186 and 188 are essentially small inline fluid accumulators with flexible, resilient walls designed to simulate the human body's vascular compliance by aiding the system in more accurately mimicking blood flow in the human body, for example, by providing flow back-pressure and/or by filtering/reducing fluid pressure spikes due, for example, to flow rate changes and/or the pumping of the pump 106. The compliance chamber 184 is located between an output 112a of the mode valve 112 and the reservoir 160 and operates in combination with an adjustable clamp 190 during normal flow mode to provide back pressure to the aorta to cause perfusion fluid to flow into the coronary sinus to feed the heart 102. The compliance chamber 186 is located between an output 112b of the mode valve 112 and the pulmonary vein cannulation interface of the organ chamber assembly 104. The primary function of the compliance chamber 186 is to provide back-pressure to the left atrium and to smooth pressure/flow spikes caused from the pumping action of the perfusion fluid pump 106, which delivers blood to the heart without causing substantial fluid pressure spikes. The compliance chamber 188 is located between an output of a one way valve 310 and an inlet 110a of the heater 110. The primary function of the compliance chamber 188 is also to smooth pressure/flow spikes caused by the pumping action of the perfusion fluid pump 106.

Figure 2:
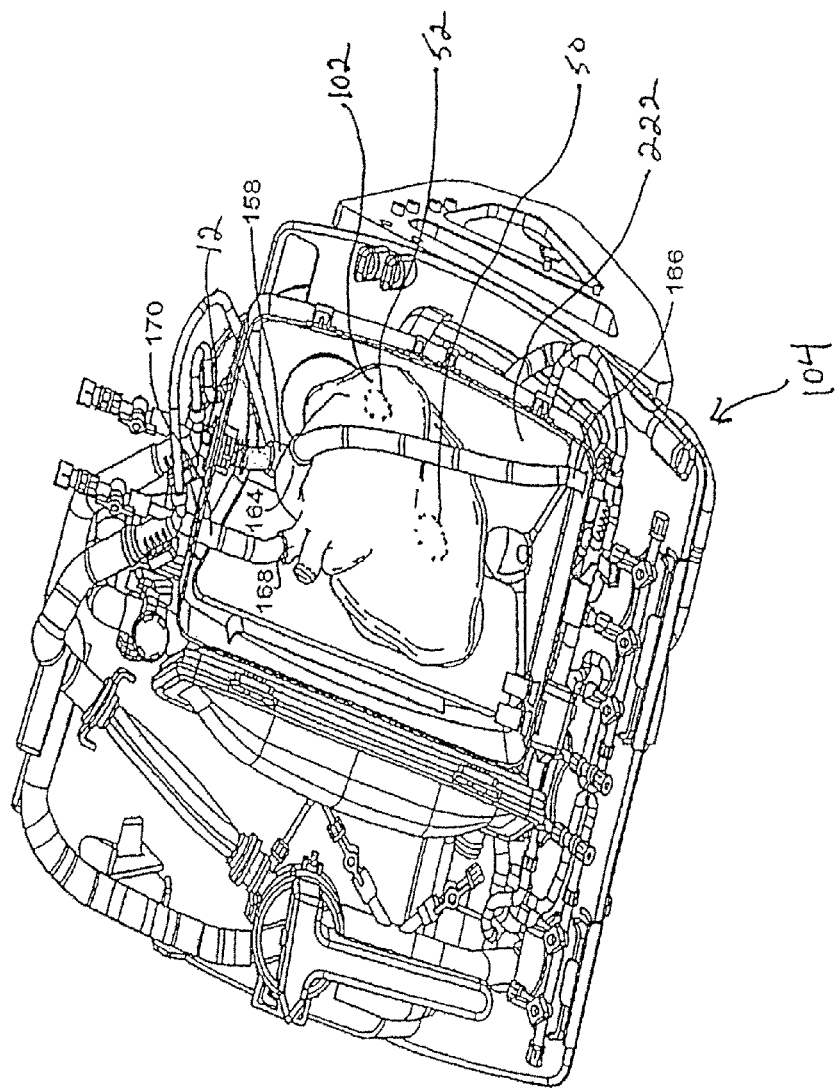
FIG. 2 illustrates an embodiment of an organ chamber assembly of the type employed in the organ care system of FIGS. 1 and 3.

FIG. 2 depicts an embodiment of an organ chamber assembly 104 of the type employed in the organ care system of FIG. 1. After explantation, an explanted heart 102 is perfused and transported to a donor site under sterile conditions while being monitored by a plurality of electrodes.

The heart rests and is supported by a foam pad or sac 222, preferably made of a biocompatible material resilient enough to cushion the heart 102 from vibrations and shocks during transport. In a preferred embodiment, the foam pad or sac 222 is comprised of silicone, although other biocompatible materials are envisioned. For reference, the heart is placed in a posterior arrangement, with the right atria in the top right and the left ventricle in the left-bottom. As shown, a right atrium electrode 52 and left ventricle electrode 50 are placed epicardially on the explanted heart 102 and are held in place by the weight of the heart 102 against the foam pad or sac 222. In a preferred embodiment, at least one side of at least one of the right atrial electrode 52 and left ventricle electrode 50 are over-molded with silicone, and friction created by the contact between the silicone over-molding of the at least one electrode and the silicone pad or sac 222 further aids in maintaining the epicardial placement of the electrode. The structure of the electrode is described in more detail below.

At least one of the right atrial electrode 52 and the left ventricle electrode 50 may be electrodes 142 and 144, described in U.S. application Ser. No. 11/246,902.

An aortic electrode 12 is placed in the aortic bloodpath for use in detecting ECG signals from the heart 102 during transport as blood travels to or from the aorta 158. The organ chamber assembly 104 includes apertures for the pulmonary artery interface 166, which carries perfusion fluid 108 from the pulmonary artery 164, and the pulmonary vein interface 170, which carries perfusion fluid to the pulmonary vein 168.

Figure 3:
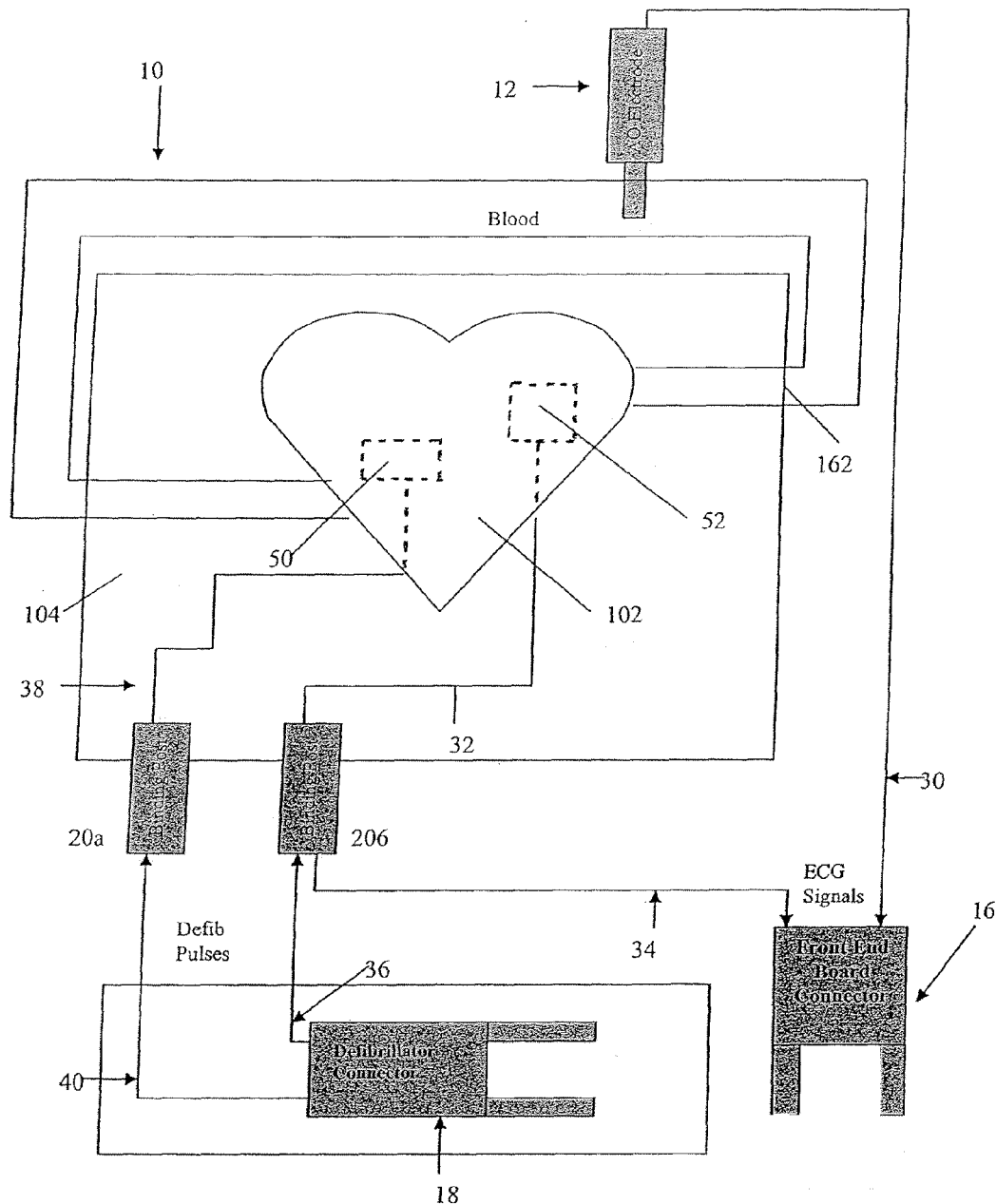
FIG. 3 illustrates an embodiment of an interconnection of the electrodes and signals flows of a system for monitoring organ electrical activity.

FIG. 3 depicts an interconnection of the electrodes and signal flows for monitoring organ electrical activity in a perfusion system 10. In a preferred embodiment, the system 10 allows monitoring of heart 102 [the heart is there, just need to add 102 to the figure] electrical activity in a perfusion system as well as the delivery of defibrillation energy or pacing signals. The system 10 includes three electrodes: a right atrial electrode 52, a left ventricle electrode 50 and an aortic electrode 12.

The aortic electrode 12 is placed in the aortic blood path outside the organ chamber 102, which provides a stable position from which ECG signals from the heart may be measured and is less susceptible to the electrode shifting due to movements from the beating heart or the vibrations in the system during transport. The right atrial electrode 52 and left ventricle electrode 50 are placed epicardially on the heart within the organ chamber. Reference to "epicardially" includes, but is not limited to, on or near the heart. A silicone covering on at least a portion of the right atrial electrode 52 and the left ventricle electrode 50 aids in providing a non-slip surface to maintain the position of the electrodes.

According to one feature of the embodiment, the perfusion-fluid contacting components may be coated or bonded with heparin or other anticoagulant or biocompatible material to reduce the inflammatory response that may otherwise arise when the perfusion fluid contacts the surfaces of the components.

In a preferred operation, ECG signals are detected by both the aortic electrode 12 and the right atrial electrode 52. An electric circuit is completed between the aortic electrode 12, through the blood and heart muscle, to the right atrial electrode 52. This placement allows more variability in the placement of the right atrial electrode 52 within the organ chamber 104 to accommodate differently shaped and sized hearts while maintaining a completed circuit.

In addition, using two epicardially placed electrodes within the organ chamber 104 to detect ECG signals from the heart 102 increases the likelihood that the electrodes would touch due to being placed in an improper position or from shifting during transport, a possibility which is eliminated by the preferred configuration. In a preferred embodiment, the right atrial electrode 52 is at least partially held in place by the weight of the heart 102, which further aids in maintaining a completed circuit for detecting ECG signals.

Electrical connection is made by placing the heart 102 on the one or more electrodes. One advantage of the invention is that it does not require the electrodes to be permanently or temporarily sutured or otherwise mechanically connected to the heart 102. However, one skilled in the art would recognize circumstances in which such a connection is desirable. The present invention can be equally useful in such circumstances.

In certain embodiments, one or more electrodes are provided for placement in the bloodpath and one or more electrodes are provided for epicardial placement on an explanted heart. In these embodiments, ECG signals may be received by varying circuits comprising two electrodes placed in the bloodstream, two electrodes placed epicardially on the explanted heart, one electrode in the bloodstream and one electrode placed epicardially on the explanted heart, or any combination of the above. One of ordinary skill in the art will recognize that two electrodes are required to measure ECG signals, and as such, numerable combinations of electrode placements will provide ECG measurements.

After explantation, defibrillation energy and/or pacing signals may be necessary to restore a normal heart beat during transport to a donor site. In addition to detecting ECG signals from the heart 102, the right atrial electrode 52, in conjunction with a left ventricle electrode 50, may be used to provide defibrillation energy and/or pacing signals to the explanted heart 102. In operation, after a normal heart rhythm is achieved by delivering a defibrillation energy and/or pacing signals to the heart 102, the left ventricle electrode 50 may be removed from the heart 102 by manipulating the electrode through the flexible membrane. Removing the electrode reduces the likelihood of irritation to the heart tissue during transport. However, it is envisioned in certain embodiments, that an operator may allow the left ventricle electrode 50 to remain epicardially placed should further defibrillation energy and/or pacing signals be required and without further need of manipulating the heart 102 and or electrodes 50 and 52.

A front end board connector 16 is provided as an interface between at least one electrode and one or more subsystems of the system 10. At least one binding post 20, is provided to allow electrical connections to at least one electrode within the heart chamber 104 while maintaining the sterile integrity of the chamber. The aortic electrode 12 is connected to the front end board connector 16 by a first wire 30. The right atrial electrode 52 is connected to a binding post 20b by a second wire 32, which is connected to the front end board connector by a third wire 34. This connection configuration allows a completed circuit for the measurement of ECG signals from the explanted heart 102. One of ordinary skill in the art will recognize that various other connections utilizing either fewer electrodes, wires or both could be used to achieve the same electrical circuit.

A defibrillator connector 18 is provided as an interface between at least one electrode and a defibrillation source for providing defibrillation energy and/or pacing signals to the heart 102. The right atrial electrode 52 is connected to a binding post 20b by a second wire 32, which is connected to the defibrillator connector 18 by a fourth wire 36. The left ventricle electrode 50 is connected to a binding post 20a by a fifth wire 38, which is connected to the defibrillator connector 18 by a sixth wire 40. This connection configuration allows a completed circuit for the delivery of defibrillation energy and/or pacing signals to the explanted heart 102. One of ordinary skill in the art will recognize that various other connections utilizing either fewer electrodes, wires or both could be used to achieve the same electrical circuit.

In a preferred embodiment, at least one of the first wire 30, third wire 34, fourth wire 36, and sixth wire 40 is a custom-made wire preferably comprised of tinned soft copped with a PVC jacket. At least one of the third wire 34, fourth wire 36, fifth wire 38, and sixth wire 40 is modified for purposes of defibrillation.

Figure 4A:
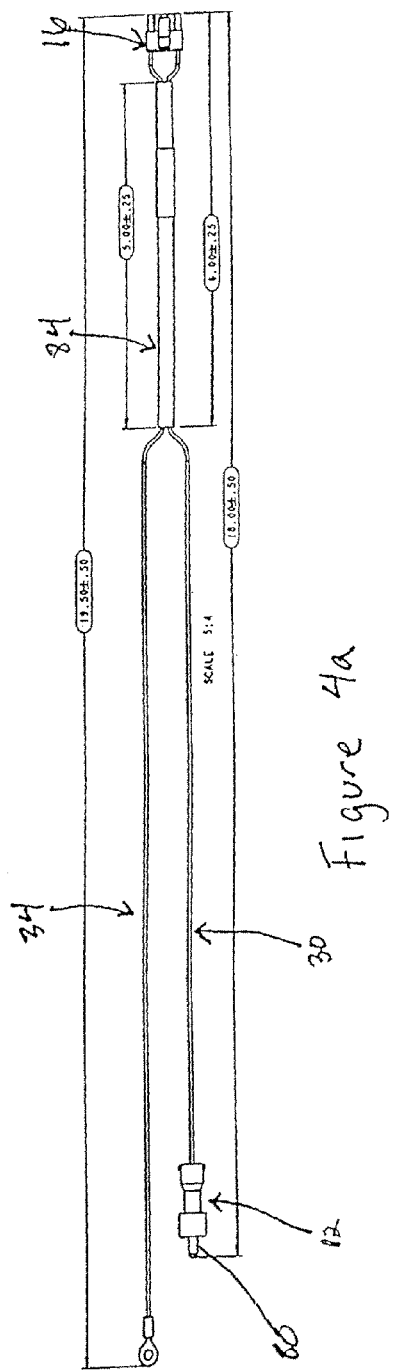
FIG. 4a illustrates an embodiment of an aortic electrode and interconnections for a an interface to a system for monitoring organ electrical activity.
Figure 4B:
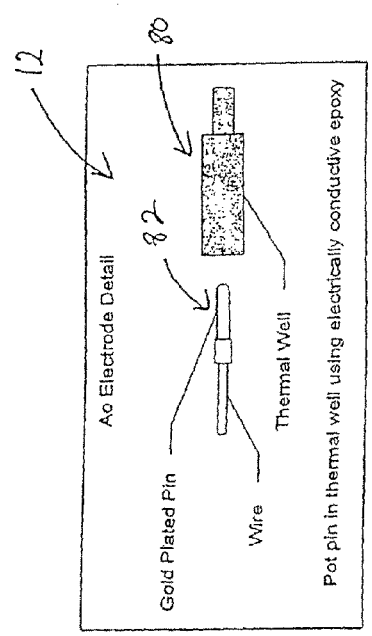
FIG. 4b illustrates an exploded view of an embodiment of an aortic electrode.

FIGS. 4a and 4b depicts an embodiment of an aortic electrode and various interconnections that may be used to connect to the system.

As best seen in FIG. 4b, an aortic electrode 12 is comprised of a thermal well 80 comprised of 304 stainless steel and polycarbonate, into which a gold plated pin 82 has been potted using electrically conductive epoxy. In a preferred embodiment, the epoxy must cure for two hours at 65° C. to fully cure. In other embodiments, it is envisioned that the aortic electrode may be comprised of other electrically conductive and biocompatible materials.

Referring to FIG. 4a, the aortic electrode is connected to a first wire 30. In a preferred embodiment, the first wire 30 and a third wire 34 are twisted together for approximately six inches and are covered in a heat shrink jacket 84.

Figure 5A:
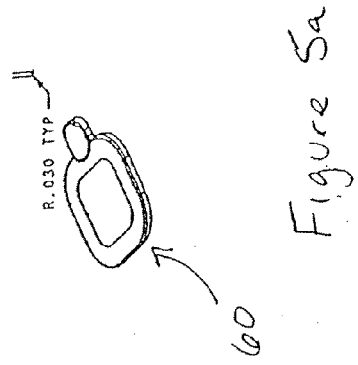
FIG. 5a illustrates an embodiment of an electrode for epicardial placement.
Figure 5B:
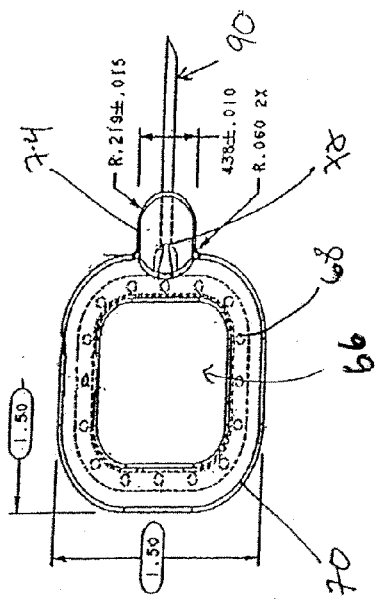
FIG. 5b illustrates a first side of an electrode for epicardial placement.
Figure 5C:
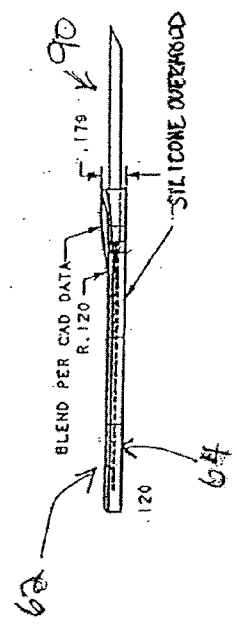
FIG. 5c illustrates a perspective view of an electrode for epicardial placement.

FIGS. 5a-c illustrate one embodiment of an electrode 60 for epicardial placement.

In a preferred embodiment, the epicardial electrodes are comprised of 304 stainless steel and over-molded with silicone. At least one aperture 68 in the stainless steel is provided to aid in securing the silicone to the stainless steel. The metal surface of the stainless steel is passivated to increase electrical performance, provide corrosion resistance and improve biocompatibility. Reference to "over-molded" includes, but is not limited to, covering or partially covering the electrode by means of molding, or other process that results in an electrode at least partially surrounded with silicone. Each epicardial electrode is resistance welded to 304 stainless steel wire 90 at a weld point 72, which is surrounded with silicone and which is terminated in a gold plated pin. In a preferred embodiment, the over-molding of the wire 90 and the electrode 60 is overlapped at an interface 74 to reduce stress on the wire at the welding point but maintain wire flexibility.

The electrode 60 is approximately a one inch by one inch square (2.5 cm by 2.5 cm), with a rounded edge 70 to reduce irritation to the tissue. It is large enough to easily contact at least part of the critical heart area and small enough to not have two electrodes touch, particularly on a small heart. These dimensions allow the electrodes to be placed precisely as well as maintain sufficient current density, i.e. keep it below damage threshold, although other electrode sizes and shapes are contemplated. In alternative embodiments, it is envisioned that each of the epicardial electrodes and wire may be comprised of other electrically conductive materials and biocompatible materials.

Referring to FIGS. 5b and 5c, in a preferred embodiment, the electrode 60 is provided with a first side 62 and a second side 64. In one configuration, a portion 66 of the first side of the electrode 60 is exposed such that an electrical connection may be made epicardially with the heart 102 by placing the heart 102 on the first side 62. The second side 64 of the electrode 60 is over-molded with silicone such that it is electrically insulated. In a preferred embodiment, the silicone is General Electric LIM 6050 silicone with 50 Shore A hardness, or other similar silicones from Wacker, Bayer or Dow Corning. 304 stainless steel and silicone are chosen for their biocompatibility as well as resistance to fluids. Further, the materials chosen are also sufficiently resistant to the sterilization process (ETO) and to vacuum. Specifically, other materials (e.g., non-pourous foams) used for electrode pads have experiences bending and deformation during an ETO sterilization process or biocompatibility issues (e.g. silver-silver chloride).

The silicone over-molding of the electrode 60 provides a non-slip surface when the electrode is placed against the pad or sac 222, which may also be constructed of silicone or have a surface that allows a reduced likelihood of slipping, which preferably aids in maintaining the positioning of the electrode after it has been epicardially placed on the heart 102.

Referring to FIG. 6, a schematic view of the fourth wire 36 and sixth wire 40 is depicted. In an alternative embodiment, the wires are comprised of tinned soft copper wire 90 with PVC insulation or heat shrink tubing 92, illustrated in FIGS. 6a and 6b. Heat shrink tubing shown in exaggerated scale. Ring connectors 94 are provide to allow multiple connectors to the cabling. A connector 96 is provided for interconnection with the system 10. In a preferred embodiment, the connector 96 is the defibrillator connector 18. In a preferred embodiment, the cabling is modified for delivering defibrillation energy and/or pacing signals.

Referring to FIG. 7, a schematic view of an embodiment of at least one of the second wire 32 and the fifth wire 38 is shown. In one embodiment, at least one of the second wire 32 and fifth wire 38 is 304 stainless steel wire 90 over-molded with silicone insulation 92. In a preferred embodiment, at least one of the second wire 32 and the fifth wire 38 is twenty gauge, multi-stranded soft-type 304 stainless steel and is over-molded with a 0.2 mm thick layer of silicone insulation.

Figure 8:
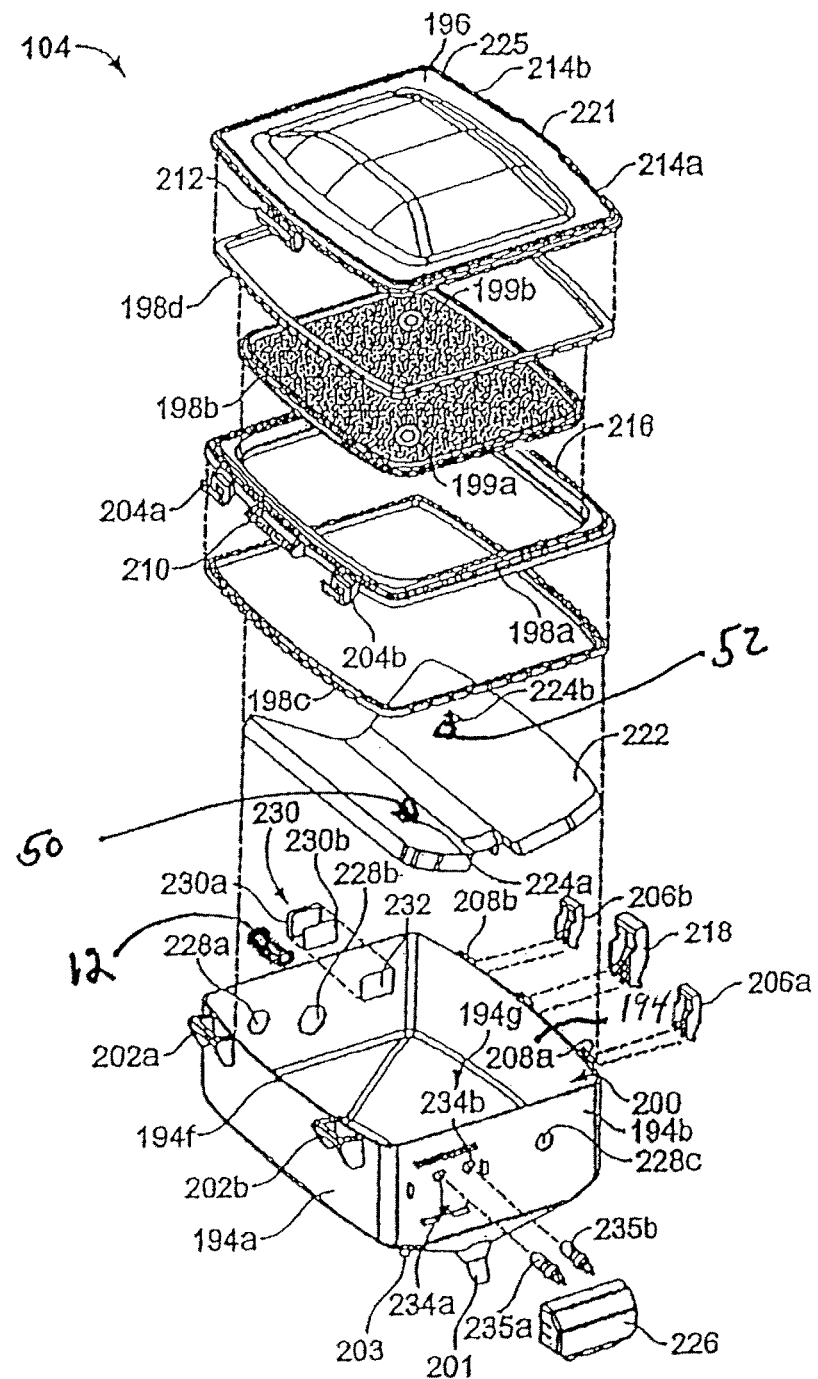
FIG. 8 illustrates an exploded view of an organ chamber assembly for use in a system for monitoring organ electrical activity; and, FIG. 9 illustrates the placement of an explanted heart on a pad containing electrodes for epicardial placement.

FIG. 8 depicts an exploded view of the illustrative organ chamber assembly 104 of FIGS. 1, 2 and 3. The organ chamber assembly 104 includes a housing 194, an outer lid 196 and an intermediate lid 198. The housing includes a bottom 194g and one or more walls 194a-194d for containing the heart 102. The intermediate lid 198 covers an opening 200 to the housing 194 for substantially enclosing the heart 102 (not shown) within the housing 194. The intermediate lid 198 includes a frame 198a and a flexible membrane 198b suspended within the frame 198a. The flexible membrane 198b, preferably, is transparent but may be opaque, translucent, or substantially transparent.

According to one feature, the flexible membrane includes sufficient excess membrane material to contact the heart 102 when contained within the housing 194. This feature enables a medical operator to touch/examine the heart 102 indirectly through the membrane 198b, or apply an ultrasound probe to the heart 102 through the membrane 198b, while maintaining sterility of the housing 194. The membrane 198b may be made, for example, from any suitable flexible polymer plastic, for example polyurethane. Apertures 199a and 199b in the membrane 198b are provided through which electrodes 50 and 52 may be fed.

The outer lid 196 opens and closes over the intermediate lid 198 independently from the intermediate lid 198. Preferably, the outer lid 196 is rigid enough to protect the heart 102 from physical contact, direct or indirect. The outer lid 196 and the chamber 194 may also be made from any suitable polymer plastic, for example polycarbonate.

According to one implementation, the housing 194 includes two hinge sections 202a and 202b, and the intermediate lid frame 198a includes two corresponding mating hinge sections 204a and 204b, respectively. The hinge sections 202a and 202b on the housing 194 interfit with the hinge sections 204a and 204b on the intermediate lid frame 198a to enable the intermediate lid 198 to open and close relative to the opening of the housing 194. The organ chamber assembly 104 also includes two latches 206a and 206b for securing the intermediate lid 198 closed over the opening 200. The latches 206a and 206b rotatably snap fit onto latch hinge section 208a and 208b, respectively, of the housing 194.

The intermediate lid frame 198a also includes a hinge section 210. The hinge section 210 rotatably snap fits with a mating hinge section 212 on the outer lid 196 to enable the outer lid 196 to open without opening the intermediate lid 198. The outer lid 196 also includes two cutouts 214a and 214b for enabling the latches 206a and 206b to clamp down on the edge 216 of the intermediate lid frame 198a.

The organ chamber assembly 104 also includes a latch 218, which rotatably snap fits onto a hinge part (not shown) on the wall 194c of the housing 194. In operation, the latch 218 engages a tab 221 on the edge 225 of the outer lid 196 to secure the outer lid 196 closed over the intermediate lid 198. The intermediate lid also includes two gaskets 198c and 198d. The gasket 198d interfits between a periphery of the intermediate lid frame 198a and a periphery of the outer lid 196 to form a fluid seal between the intermediate lid 198 and the outer lid 196 when the outer lid 196 is closed. The gasket 198c interfits between an outer rim 194f of the housing 194 and the intermediate lid frame 198a to form a fluid seal between the intermediate lid 198 and the periphery 194f of the housing 194 when the intermediate lid 198 is closed, thereby providing a sterile environment for the heart once the organ care system is removed from the sterile operating room.

Optionally, the organ chamber assembly 104 includes a pad 222 or a sac assembly sized and shaped for interfitting over an inner bottom surface 194g of the housing 194. Preferably, the pad 222 is formed from a material resilient enough to cushion the heart 102 from mechanical vibrations and shocks during transport, for example a silicone foam.

Again referring to FIG. 8, according to an illustrative embodiment, the mechanism includes two through-apertures 224a and 224b for passing electrical leads from the under side of the pad 222 to corresponding electrodes on the heart-contacting surface of the pad. Passing the electrical leads through the pad 222 to the electrodes enables the electrodes to be adjustably positioned within the pad 222 to accommodate variously sized hearts. In other embodiments, the mechanism may include, without limitation, one or more differently oriented slots, indentations, protrusions, through apertures, partially through apertures, hooks, eyelets, adhesive patches, or the like. In certain embodiments, the pad 222 may be configured with one or more sleeve-like structures that allow an electrode to be inserted within the pad 222, thus providing a membrane-like surface of the pad 222 positioned between the electrode and the heart 102.

In some illustrative embodiments, the pad 222 is configured as a pad assembly, with the assembly including one or more electrodes, such as the electrodes 50 and 52, adjustably located in or on the pad 222. According to one advantage, the pad/electrode configuration of the invention facilitates contact between the electrodes and the heart 102 placed on the pad 222, without temporarily or permanently suturing or otherwise mechanically connecting the electrodes to the heart 102. The weight of the heart 102 (illustrated in FIG. 9) itself can also help stabilize the electrodes during transport.

As shown in FIG. 8, the organ chamber assembly 104 includes electrical interface connections 235a-235b, which mount into the apertures 234a-234b, respectively, in the wall 194b of the housing 194. A cover 226 is provided for protecting the electrical interface connections 235a-235b. In a preferred embodiment, the electrical interface connections 235a-235b are at least one of the binding posts 20a-b of FIG. 3.

The interface connections 235a and 235b and aorta electrode 12 couple electrical signals, such as ECG signals, from the electrodes out of the housing 194, for example, to a controller and/or an operator interface. According to one embodiment, the electrodes couple to the controller and/or the operator interface via the front end board connector 16 (not shown). The interface connections 235a and 235b may also couple to a defibrillation source, which may be either provided by external instrumentation or through circuitry within the system 10, and which can send a defibrillation and/or pacing signal through electrodes to the heart 102. According to one embodiment, the interface connections 235a and 235b are coupled to a defibrillation source via the defibrillation connector 18.

Still referring to FIG. 8, the organ chamber assembly 104 includes a resealable membrane interface 230, which mounts in an interface aperture 232. The interface 230 includes a frame 230a and a resealable polymer membrane 230b mounted in the frame 230a. The membrane 230b may be made of silicone or any other suitable polymer. In operation, the interface 230 is used to provide pacing leads, when necessary, to the heart 102, without having to open the chamber lids 196 and 198. The membrane 230b seals around the pacing leads to maintain a closed environment around the heart 102. The membrane 230b also reseals in response to removing the pacing leads.

The organ chamber assembly also includes a drain 201 for draining perfusion fluid 108 out of the housing 194 back into the reservoir 160. Further, at least one mounting receptacle 203 is provided for mounting the organ chamber assembly 104 onto further components of the system 10. As well, a plurality of apertures 228a-c located on the organ chamber assembly 104 are provided for cannulation to vascular tissue of the heart 102.

Figure 9:
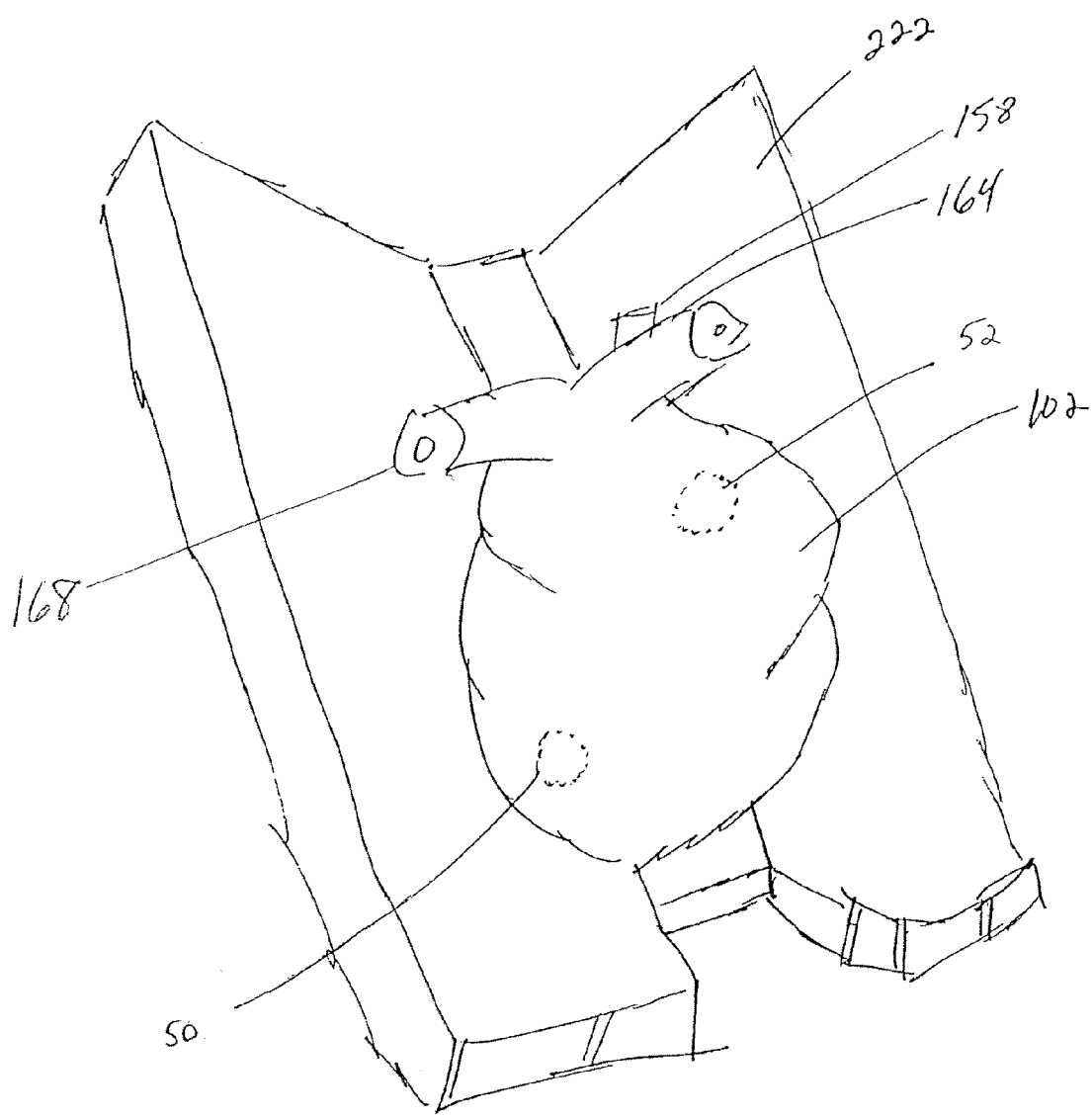

FIG. 9 depicts the placement of an explanted heart on a pad containing electrodes for epicardial placement. At least one of the right atrial electrode 52 and the left ventricle electrode 50 are at least partially held in place by the weight of the explanted heart 102 against the pad 222. As shown, the pulmonary artery 164, aorta 158, and pulmonary vein 168 are presented for cannulation.

Operationally, according to one embodiment, the heart 102 is harvested from a donor and cannulated into the organ chamber assembly 104. The perfusion fluid 108 is prepared for use within system 10 by being loaded into the reservoir 160 via portal 774 and, optionally, being treated with therapeutics via portal 762. The pump 106 pumps the loaded perfusion fluid 108 from a reservoir 160 to the heater assembly 110. The heater assembly 110 heats the perfusion fluid 108 to or near a normal physiological temperature. According to another aspect, embodiments of the disclosed subject matter are directed to a method of perserving a heart ex vivo, the method including the steps of placing a heart on one or more electrodes in a protective chamber of portable organ care system, pumping a perfusion fluid to the heart, the perfusion fluid being at a temperature of between about 25° C. and about 37° C., and at a volume of between about 200 ml/min and about 5 L/min, and monitoring electrical signals from the electrodes while pumping the perfusion fluid to the heart to preserve the heart ex vivo. According to one embodiment, the heater assembly 110 heats the perfusion fluid to between about 32° C. and about 37° C. The heater assembly 110 has an internal flow channel with a cross-sectional flow area that is approximately equal to the inside cross-sectional area of fluid conduits that carry the perfusion fluid 108 into and/or away from the heater assembly 110, so as to minimize disturbance of fluid flow. From the heater assembly 110, the perfusion fluid 108 flows to the flow mode selector valve 112.

One or more electrical signals related to the activity of the heart 102, i.e., ECG signals, are received by one or more electrodes 50 and 52 placed epicardially on the explanted heart 102. The one or more electrical signals are transmitted along at least one wire 32 and 38 inside the organ chamber to one or more binding posts 20a-b located at an interface between the inside of the organ chamber 104 and the outside of the organ chamber. This binding post configuration allows one or more signals to enter and exit the organ chamber 104 while maintaining the sterile environment within the organ chamber during transport of the explanted organ.

The binding posts 20a and 20b may send or receive one or more signals to one or more units, systems, controllers or the like for the maintenance of the heart 102. In one embodiment, one or more signals from electrodes 50 and 52 placed epicardially on an explanted heart 102 are transmitted to the binding posts 20a-b at the interface of the organ chamber 104 and are received by a front end board connector 16, which may be connected to one or more units, systems or controllers for measuring signals from the explanted heart 102 and providing responses to the one or more signals. In some embodiments, the one or more signals received by the front end board connector 16 are used to determine at least one of, but not limited to, the rate of a pump for providing perfusion fluid to the explanted heart 102, the temperature to which the heating elements inside the heater should be set, determining whether pacing signals to maintain regular heart rhythm are required, the timing of pacing signals to be delivered to the heart 102, etc.

According to another advantage of the present invention, the binding posts 20a,b may send or receive at least one signal to a defibrillator connector 18. According to one embodiment, the defibrillator connector 18 sends signals to the binding posts 20a-b, which are received by electrodes placed epicardially on an explanted heart 102. It is contemplated that in some embodiments, the electrodes are a right atrial electrode 52 and a left ventricle electrode 50. In some embodiments, the signals sent by the defibrillator connector 18 are pacing signals for maintaining a proper heart 102 rhythm of the explanted heart 102.

According to another embodiment of the present invention, signals received by the front end board connector 16 are transduced and analyzed; the analysis determining at least one output signal from the defibrillator connector 18 to be transmitted to an explanted heart 102 by the binding posts 20a-b and electrodes placed on the explanted heart 102, respectively.

In the previous description, reference is made to the accompanying drawings that form a part of the present disclosure, and in which are shown, by way of illustration, specific embodiments of the invention. These embodiments are described in sufficient detail to enable those skilled in the art to practice the invention, and it is to be understood that other embodiments may be utilized and that structural and other changes may be made without departing from the scope of the present invention. The present disclosure is, therefore, not to be taken in a limiting sense. The present disclosure is neither a literal description of all embodiments of the invention nor a listing of features of the invention that must be present in all embodiments.

Numerous embodiments are described in this patent application, and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with various modifications and alterations. Although particular features of the present invention may be described with reference to one or more particular embodiments or figures, it should be understood that such features are not limited to usage in the one or more particular embodiments or figures with reference to which they are described.

The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

The terms "a", "an" and "the" mean "one or more", unless expressly specified otherwise.

Headings of sections provided in this patent application and the title of this patent application are for convenience only, and are not to be taken as limiting the disclosure in any way.

Other embodiments, extensions, and modifications of the ideas presented above are comprehended and within the reach of one skilled in the art upon reviewing the present disclosure. Accordingly, the scope of the present invention in its various aspects should not be limited by the examples and embodiments presented above. The individual aspects of the present invention, and the entirety of the invention should be regarded so as to allow for modifications and future developments within the scope of the present disclosure. The present invention is limited only by the claims that follow.

What is claimed is:

1. An organ care system for maintaining an explanted heart at a near physiologic condition using perfusion fluid and which allows for sending electrical signals to and from the explanted heart, the system comprising:
   a heater assembly configured to heat the perfusion fluid;
   a first electrode placed in an aortic bloodstream conduit and connected to the organ care system for receiving signals from the explanted heart;
   a second electrode connected to the organ care system for receiving signals from the explanted heart and sending signals thereto;
   a third electrode connected to the organ care system for sending signals to the explanted heart; and
   a controller that:
      receives a signal from at least one of the first and second electrodes and determines whether to provide pacing signals to maintain the explanted heart based on the signal received from the at least one of the first and second electrodes, and
      controls the heater assembly to maintain the heart at a temperature between 26° and 37° C. using the perfusion fluid,
   wherein at least one of the second and third electrode is in a sterile environment.

2. The organ care system of claim 1, wherein each of the second electrode and third electrode is configured to be placed on the explanted heart.

3. The organ care system of claim 1, wherein at least a portion of at least one of the second electrode and third electrode is covered with silicone.

4. The organ care system of claim 1, wherein the signals are at least one of ECG signals, defibrillation signals, and pacing signals.

5. The organ care system of claim 1, wherein the sterile environment further comprises a housing which encloses the explanted heart and into which a conduit delivers perfusion fluid which passes through the explanted heart.

6. The organ care system of claim 5, wherein the housing further comprises a pad, wherein the pad is configured to receive an explanted heart so that when the explanted heart is beating at a normal physiologic rate it is maintained in a stable position within the housing.

7. The organ care system of claim 6, wherein at least one of the second electrode and the third electrode is held in place against the pad by the weight of the heart.

8. The organ care system of claim 1 wherein the first one of the electrodes further comprises:
an electrically conductive pin placed within a bloodpath of an organ care system;
a wire for electrically coupling the electrode to the organ care system;
wherein the wire and the pin are physically and electrically connected by a conductive epoxy.

9. The organ care system of claim 1,
wherein the first electrode is configured to receive ECG signals from the explanted heart; and wherein the system further comprises
a right atrial electrode connected to the organ care system for epicardial placement on the explanted heart; and
wherein the right atrial electrode is configured to receive ECG signal from the explanted heart.

10. The system of claim 1, wherein the controller
controls the heater assembly to maintain the heart at a temperature between 32° and 37° C.

11. An organ care system for maintaining an explanted heart at a near physiologic condition using perfusion fluid, the system comprising:
a heater assembly configured to heat the perfusion fluid;
a first electrode connected to the organ care system for receiving signals from an explanted heart,
wherein the first electrode is placed in the aortic bloodstream of the explanted heart;
a second electrode connected to the organ care system for receiving signals from the explanted heart and sending signals thereto,
wherein the second electrode is configured to be placed on the explanted heart adjacent the right atria;
a third electrode connected to the organ care system for sending signal to the explanted heart,
wherein the third electrode is configured to be placed epicardially on the explanted heart adjacent the left ventricle when the explanted heart is maintained at a near physiologic condition; and
a controller that:
receives a signal from at least one of the first and second electrodes and determines whether to provide pacing signals to maintain the explanted heart based on the signal received from the at least one of the first and second electrodes, and
controls the heater assembly to maintain the heart at a temperature between 26° and 37° C. using the perfusion fluid.

12. The organ care system of claim 11, wherein at least a portion of the second and third electrode is covered with silicone.

13. The organ care system of claim 11, wherein the system further comprises a pad, wherein the pad is configured to receive the explanted heart so that the explanted heart is maintained in a stable position within the housing.

14. The organ care system of claim 13, wherein at least one of the second electrode and the third electrode is held in place against the pad by the weight of the heart.

15. The organ care system of claim 11, wherein an electrical circuit is completed between the first electrode and the second electrode utilizing as a conductor at least one of a perfusion fluid and the heart.

16. The system of claim 11, wherein the controller
controls the heater assembly to maintain the heart at a temperature between 32° and 37° C.

17. An apparatus for maintaining an explanted heart at a near physiologic condition using perfusion fluid, the apparatus comprising:
a heater assembly configured to heat the perfusion fluid;
a first electrode placed in the aortic bloodstream of an explanted heart,
wherein the first electrode is comprised of at least one of stainless steel and polycarbonate;
a second electrode for epicardial placement on the explanted heart;
a third electrode for epicardial placement on the explanted heart;
a controller that:
receives a signal from at least one of the first, second and third electrodes, and determines whether to provide pacing signals to maintain the explanted heart based on the signal received from the at least one of the first, second and third electrodes, and
controls the heater assembly to maintain the heart at a temperature between 26° and 37° C. using the perfusion fluid;
wherein at least one of the second electrode and third electrode is comprised of stainless steel,
wherein at least a portion of at least one of the second electrode and third electrode is covered by silicone; and
wherein at least one of the first electrode, second electrode and third electrode is configured to send and receive signals to the explanted heart while the heart is at a near physiologic condition.

18. The apparatus of claim 17, wherein at least one of the second and third electrode is held in place against a pad by the weight of the explanted organ heart so that the explanted heart is maintained in a stable position within the housing.

19. The apparatus of claim 18, wherein the pad is at least partially comprised of silicone, and
wherein at least one of the second and third electrode is at least partially held in place by friction.

20. The apparatus of claim 17, wherein the first electrode further comprises silicone.

21. The system of claim 17, wherein the controller
controls the heater assembly to maintain the heart at a temperature between 32° and 37° C.

22. An organ care system for maintaining an explanted organ at a near physiologic condition, the system comprising:
a silicone pad defining an aperture and being configured to be in contact with the explanted organ;
a chamber configured to hold the explanted organ;
a heater assembly configured to heat perfusion fluid;
a first electrode disposed in an aortic bloodstream conduit coupled to the chamber that receives electrical signals from the explanted organ;
a second electrode disposed in the chamber and that contacts the explanted organ through the aperture in the silicone pad when the explanted organ is placed in the chamber;
a controller that:
receives a signal from at least one of the first and second electrodes and to determines whether to provide pacing signals to maintain the explanted heart based on the signal received from the at least one of the first and second electrodes, and
controls the heater assembly to maintain the explanted organ at a temperature between 26° and 37° C. using the perfusion fluid.

23. The organ care system of claim 22, wherein the second electrode is configured to send and receive signals to an explanted heart.

24. The organ care system of claim 23, wherein the second electrode is at least partially held in place against the explanted organ by the weight of the explanted organ.

25. The organ care system of claim 22, wherein the second electrode is at least partially held in place on the silicone pad by friction.

26. The system of claim 22, wherein the controller controls the heater assembly to maintain the explanted organ at a temperature between 32° and 37° C.

27. An organ care system for maintaining an explanted heart at a near physiologic condition using perfusion fluid, the system comprising:
   a heater assembly configured to heat perfusion fluid;
   an aortic electrode connected to the organ care system placed in an aortic bloodpath of an explanted heart, wherein the aortic electrode is configured to receive electrocardiogram (ECG) signals from the explanted heart;
   a right atrial electrode connected to the organ care system for epicardial placement on the explanted heart, wherein the right atrial electrode is configured to receive ECG signal from the explanted heart, and wherein the right atrial electrode is configured to send to the explanted heart at least one of defibrillation energy and pacing signals;
   a left ventricle electrode connected to the organ care system for epicardial placement on the explanted heart, wherein the left ventricle electrode is configured to send to the explanted heart at least one of defibrillation energy and pacing signals; and
   a controller that:
      receives a signal from at least one of aortic and right atrial electrodes and determines whether to provide pacing signals to maintain the explanted heart based on the signal received from the at least one of the aortic and right atrial electrodes, and
      controls the heater assembly to maintain the heart at a temperature between 26° and 37° C. using the perfusion fluid.

28. The organ care system of claim 27, wherein the ECG signals received by the aortic electrode and the right atrial electrode are received by a circuit at least partially comprised of the aortic electrode, the right atrial electrode, a perfusion fluid and the explanted heart.

29. The system of claim 27, wherein the controller controls the heater assembly to maintain the heart at a temperature between 32° and 37° C.

30. An organ care system for maintaining an explanted heart at a near physiologic condition using perfusion fluid, the system comprising:
   a circuit for receiving electrocardiogram (ECG) signals from the explanted heart, wherein the circuit comprises:
      a first electrode placed in the aortic bloodpath of the explanted heart;
      a second electrode configured to be placed epicardially on the explanted heart;
      a perfusion fluid configured to perfuse the explanted heart; and
   a heater assembly configured to heat perfusion fluid;
   a controller that:
      measures the ECG signals from the explanted heart, and determines whether to provide pacing signals to maintain the explanted heart based on at least the measured ECG signal, and
      controls the heater assembly to maintain the heart at a temperature between 26° and 37° C. using the perfusion fluid.

31. The system of claim 30, wherein the controller controls the heater assembly to maintain the heart at a temperature between 32° and 37° C.

32. A method for measuring electrocardiogram (ECG) signals in an organ care system for maintaining an explanted heart at a near physiologic condition, the method comprising:
   maintaining the heart at a temperature between 26° and 37° C.;
   placing a first electrode in the aortic bloodpath of the explanted heart;
   placing a second electrode epicardially on the explanted heart;
   measuring ECG signals produced by the explanted heart using a circuit comprising at least the first and second electrodes, a perfusion fluid, and the explanted heart;
   receiving signals from the circuit; and
   determining whether pacing signals to maintain the heart are required.

33. A method for sending and receiving signals in an organ care system for maintaining an explanted heart at a near physiologic condition, the method comprising:
   maintaining the heart at a temperature between 26° and 37° C.;
   providing a perfusion fluid to the explanted heart;
   providing a defibrillation source;
   placing at least a first electrode in the aortic bloodpath of the explanted heart;
   placing a second electrode epicardially;
   placing a third electrode epicardially;
   forming a second circuit comprising the second electrode, the third electrode and the defibrillation source;
   receiving electrocardiogram (ECG) signals from a first circuit comprising the first electrode, the second electrode, and the perfusion fluid, wherein the ECG signals are measured from the explanted heart; and
   sending at least one of a defibrillation signal and a pacing signal to a second circuit comprising the second electrode, the third electrode, and the defibrillation source, to maintain the heart.

* * * * *